US012331286B2

(12) United States Patent
Ares, Jr. et al.

(10) Patent No.: US 12,331,286 B2
(45) Date of Patent: *Jun. 17, 2025

(54) METHODS OF ADDING POLYMERS TO RIBONUCLEIC ACIDS

(71) Applicant: The Regents of the University of California, Oakland, CA (US)

(72) Inventors: Manuel Ares, Jr., Santa Cruz, CA (US); Logan Mulroney, Santa Cruz, CA (US); Jenny Vo, Santa Cruz, CA (US); Mark Akeson, Santa Cruz, CA (US)

(73) Assignee: The Regents of the University of California

( * ) Notice: Subject to any disclaimer, the term of this patent is extended or adjusted under 35 U.S.C. 154(b) by 0 days.

This patent is subject to a terminal disclaimer.

(21) Appl. No.: 18/587,665

(22) Filed: Feb. 26, 2024

(65) Prior Publication Data

US 2024/0247251 A1  Jul. 25, 2024

Related U.S. Application Data

(62) Division of application No. 16/886,398, filed on May 28, 2020, now Pat. No. 11,926,819.

(60) Provisional application No. 62/853,567, filed on May 28, 2019.

(51) Int. Cl.
| C12N 9/12 | (2006.01) |
| C12N 15/10 | (2006.01) |
| C12Q 1/6809 | (2018.01) |
| C12Q 1/6869 | (2018.01) |
| C12Q 1/6876 | (2018.01) |

(52) U.S. Cl.
CPC ......... C12N 15/102 (2013.01); C12N 9/1282 (2013.01); C12Y 207/07052 (2013.01); C12Y 207/07072 (2013.01)

(58) Field of Classification Search
CPC .......... C12N 9/1282; C12Y 207/07022; C12Y 207/07052; C12Q 1/6869; G01N 27/447
See application file for complete search history.

(56) References Cited

U.S. PATENT DOCUMENTS

| 9,481,908 B2 | 11/2016 | Olasagasti et al. |
| 2014/0051068 A1 | 2/2014 | Cherf et al. |
| 2015/0197796 A1 | 7/2015 | White et al. |
| 2015/0268256 A1 | 9/2015 | Sanghera et al. |
| 2015/0344944 A1 | 12/2015 | Reid et al. |
| 2015/0346149 A1 | 12/2015 | Brown et al. |
| 2016/0010147 A1 | 1/2016 | Heron et al. |
| 2016/0251710 A1 | 9/2016 | Brown et al. |
| 2017/0002406 A1 | 1/2017 | Bowen et al. |
| 2017/0022557 A1 | 1/2017 | Clarke et al. |
| 2017/0058338 A1 | 3/2017 | Jayasinghe et al. |
| 2017/0067101 A1 | 3/2017 | Clarke et al. |
| 2017/0091427 A1 | 3/2017 | Massingham |
| 2017/0107569 A1 | 4/2017 | Heron et al. |
| 2017/0204457 A1 | 7/2017 | Crawford et al. |
| 2017/0253910 A1 | 9/2017 | Brown et al. |
| 2017/0253923 A1 | 9/2017 | Garalde et al. |
| 2017/0283470 A1 | 10/2017 | Howorka et al. |
| 2017/0326550 A1 | 11/2017 | Brown et al. |
| 2017/0335384 A1 | 11/2017 | Jayasinghe et al. |
| 2017/0363577 A1 | 12/2017 | Reid et al. |
| 2018/0030530 A1 | 2/2018 | Moysey et al. |
| 2018/0037874 A9 | 2/2018 | Bruce et al. |
| 2018/0087101 A9 | 3/2018 | Clarke et al. |

OTHER PUBLICATIONS

Chu et al. (1981) "SV40 DNA transfection of cells in suspension: analysis of the efficiency of transcription and translation of T-antigen" Gene 13:197-202.
Feng et al. (2015) "Nanopore-based Fourth-generation DNA Sequencing Technology" Genomics, Proteomics & Bioinformatics 13(1):4-16.
Lieberman et al. (2010) "Processive Replication of Single DNA Molecules in a Nanopore Catalyzed by phi29 DNA Polymerase" J. Am. Chem. Soc. 132(50):17961-17972.
Martin et al. (2007) "RNA-specific ribonucleotidyl transferases" RNA, 13:1834-1849.
Preston et al. (2019) "Unbiased screen of RNA tailing activities reveals a poly(UG) polymerase" Nat. Methods, 16(5):437-445.
Rissland et al. (2007) "Efficient RNA Polyuridylation by Noncanonical Poly(A) Polymerases" Molecular and Cellular Biology, 27(10):3612-3624.
Stoddart et al. (2009) "Single-nucleotide discrimination in immobilized DNA oligonucleotides with a biological nanopore" PNAS 106(19):7702-7707.

*Primary Examiner* — Maryam Monshipouri
(74) *Attorney, Agent, or Firm* — Brian E. Davy; Bozicevic, Field & Francis LLP

(57) ABSTRACT

Provided are methods of adding a polymer of non-canonical nucleotides to the 3' end of a ribonucleic acid (RNA). In certain embodiments, the methods comprise combining an RNA, a polynucleotide-3' nucleotidyl transferase, and non-canonical nucleotides, in a reaction mixture under conditions in which the polynucleotide-3' nucleotidyl transferase adds a polymer of the non-canonical nucleotides to the 3' end of the RNA. Such methods may further include analyzing the RNA using a nanopore. According to some embodiments, the methods include identifying the polymer of non-canonical nucleotides added to the 3' end of the RNA, and determining the junction between the 3' end of the RNA and the polymer of non-canonical nucleotides to identify the 3' end of the RNA. Kits that find use, e.g., in practicing the methods of the present disclosure are also provided.

8 Claims, 17 Drawing Sheets

Specification includes a Sequence Listing.

METHODS OF ADDING POLYMERS TO RIBONUCLEIC ACIDS

CROSS-REFERENCE TO RELATED APPLICATION

This application is a divisional of U.S. application Ser. No. 16/886,398, filed on May 28, 2020, which claims the benefit of U.S. Provisional Patent Application No. 62/853,567, filed May 28, 2019, which application is incorporated herein by reference in its entirety.

STATEMENT OF GOVERNMENT SUPPORT

This invention was made with Government support under Grant Nos. 1R01HG010053-01 and 2R01GM040478-30 awarded by the National Institutes of Health. The Government has certain rights in the invention.

INCORPORATION BY REFERENCE OF SEQUENCE LISTING PROVIDED AS A SEQUENCE LISTING XML FILE

A Sequence Listing is provided herewith as a Sequence Listing XML, UCSC-385DIV_SEQ_LIST, created on Feb. 26, 2024 and having a size of 14,520 bytes. The contents of the Sequence Listing XML are incorporated herein by reference in their entirety.

INTRODUCTION

The transcriptome consists of all the RNA molecules within a cell or cell population, which has an abundance of information that reflects the regulation of processes within the cell. A common method of studying the transcriptome is through Next Generation Sequencing (NGS) by Illumina, which analyzes RNA through sequencing-by-synthesis (SBS). SBS synthesizes new strands of modified cDNA through multiple cycles of nucleotide addition on a flowcell using 3' blocked fluorescently labeled nucleotides, allowing for detection of fluorescence for the canonical nucleotides A, C, G, and T, each attached to a different dye. The color of the fluoresce indicates the base being added, which is recorded with each cycle to determine the sequence of a DNA molecule, creating a "read". The core steps of preparing RNA for sequencing using NGS includes fragmentation of long RNA transcripts, ligation of adapters containing unique barcodes for differentiating RNA samples on the 5' and 3' ends of the RNA for hybridization onto the flowcell, reverse transcription, PCR, optional unique molecular identifiers for managing PCR bias, and subsequent wash steps for excess adapter removal from the final library.

NGS is useful for its high accuracy in reads from the SBS strategy, which allows for large scale sequencing resulting in 20-30 million reads per sample. NGS has relatively low cost by allowing for multiple samples to be sequenced in the same run by the use of barcodes for each RNA sample.

For NGS, no more than ~150 bases can be read in sequence, meaning that longer transcripts require fragmentation in order to cover most of the transcript. Computational reconstruction of the transcript is done by aligning the fragments to a reference genome. This can introduce difficulties in interpretation, such as identifying alternative splicing events, ambiguities in isoform identification, quantification, and mapping to the genome. Artefacts like template switching, where a synthesized DNA strand re-associates onto a different template, can produce chimeric cDNAs that do not represent any RNA in the sample. During reverse transcription, the reverse transcriptase may jump to a different part of the RNA strand leading to false identification of gene fusion events and spliced isoforms. The reverse transcriptase is also unable to transfer most RNA modification information onto the cDNA strand, or is actually inhibited by RNA modifications, preventing study of many RNA modifications. PCR also introduces biases by preference in amplification of shorter products resulting in number of reads not correlating to actual abundance of transcripts.

Direct-RNA sequencing from Oxford Nanopore Technologies (ONT) allows for sequencing of the native RNA without cDNA or amplification, which eliminates biases, and preserves information about each strand in the raw current measurements. Direct-RNA Nanopore sequencing also allows for sequencing of the full length of RNA transcripts. Sequencing the full length of an RNA transcript is advantageous for studying the transcriptome. For example, isoforms come from mRNAs that are transcribed from the same locus but have different transcription start sites, untranslated regions and protein coding sequencing possibly resulting in a different gene function, and RNA may also contain repeat elements. Sequencing the full length of the RNA is important for detecting these isoforms and repeat elements and makes proper alignment of these reads to the genome easier.

In Nanopore sequencing, negatively charged polynucleotides are driven towards the nanopores embedded onto a membrane through an electrical potential and are translocated using a protein motor that controls the rate of movement using ATP hydrolysis. As the RNA moves through the pore, a critical string of nucleotides (k-mer) occupies the narrowest part of the pore at a given time, reported to be five to six nucleotides for each k-mer (cite). Each k-mer produces its own unique signal, and changes in the electrical current are produced by each k-mer as each passes through the pore in sequence. Base-calling programs use these electric current measurements to interpret the sequence of the molecule based on each k-mer measurement. Direct-RNA sequencing has been used by several groups to investigate properties of RNA, for example the detection of modifications, structure analysis, and discovery of novel isoforms, and estimation of polyA tail length.

A limitation of ONT's standard direct-RNA sequencing library preparation method is that it requires a polyA enriched sample and a poly(T) adapter for RNA capture at the 3' ends, so that only the polyadenylated or poly(A)+ fraction of the transcriptome can be observed.

SUMMARY

Provided are methods of adding a polymer of non-canonical nucleotides to the 3' end of a ribonucleic acid (RNA). In certain embodiments, the methods comprise combining an RNA, a polynucleotide-3' nucleotidyl transferase, and non-canonical nucleotides, in a reaction mixture under conditions in which the polynucleotide-3' nucleotidyl transferase adds a polymer of the non-canonical nucleotides to the 3' end of the RNA. Such methods may further include analyzing the RNA using a nanopore. For example, the methods may include identifying the polymer of non-canonical nucleotides added to the 3' end of the RNA, and determining the junction between the 3' end of the RNA and the polymer of non-canonical nucleotides to identify the 3' end of the RNA. Kits that find use, e.g., in practicing the methods of the present disclosure are also provided.

DETAILED DESCRIPTION

Figure 1:
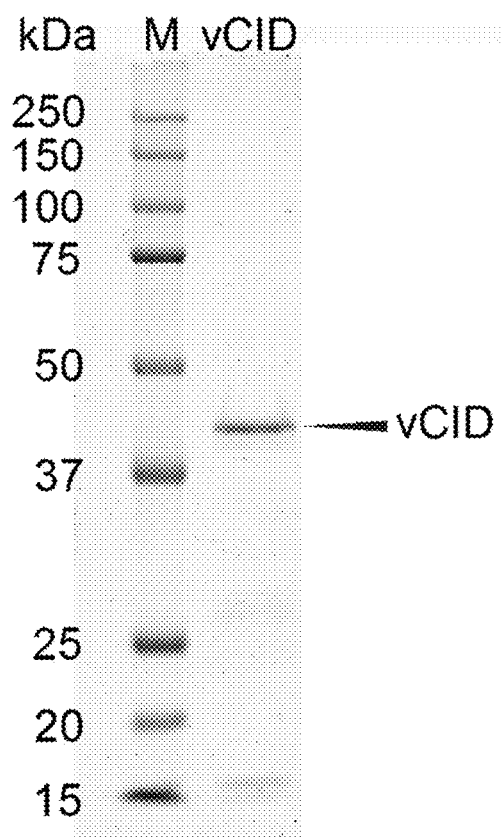
FIG. 1: Purified vCID protein visualized by SDS-PAGE.

Before the methods and kits of the present disclosure are described in greater detail, it is to be understood that the methods and kits are not limited to particular embodiments described, as such may, of course, vary. It is also to be understood that the terminology used herein is for the purpose of describing particular embodiments only, and is not intended to be limiting, since the scope of the methods and kits will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods and kits. The upper and lower limits of these smaller ranges may independently be included in the smaller ranges and are also encompassed within the methods and kits, subject to any specifically excluded limit in the stated range. Where the stated range includes one or both of the limits, ranges excluding either or both of those included limits are also included in the methods and kits.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods and kits belong. Although any methods and kits similar or equivalent to those described herein can also be used in the practice or testing of the methods and kits, representative illustrative methods and kits are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present methods and kits are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods and kits, which are, for clarity, described in the context of separate embodiments, may also be provided in combination in a single embodiment. Conversely, various features of the methods and kits, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present methods and kits and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

Methods

As summarized above, the present disclosure provides methods of adding a polymer of non-canonical nucleotides to the 3' end of a ribonucleic acid (RNA). In certain embodiments, the methods comprise combining an RNA, a polynucleotide-3' nucleotidyl transferase, and non-canonical nucleotides, in a reaction mixture under conditions in which the polynucleotide-3' nucleotidyl transferase adds a polymer of the non-canonical nucleotides to the 3' end of the RNA.

The methods of the present disclosure find use in a variety of contexts. For example, according to some embodiments, the methods enable determination of the natural 3' ends of RNAs of interest. Mapping the 3' ends of RNA molecules at nucleotide sequence resolution is a frequently encountered problem. S1 nuclease mapping is a sensitive approach for localizing 3' ends but does not allow specification of an exact end with confidence. Enzymatic labeling of the 3'-terminus of an RNA followed by RNA sequencing is applicable to RNAs that can be obtained in pure form but is not feasible when there is significant 3'-terminal heterogeneity. With respect to polyadenylated RNAs, in addition to regulating RNA degradation, poly(A) tail length has been shown to correlate with translation efficiency during embryonic development, possibly by favoring a closed-loop structure of the mRNA. Recent studies using *C. elegans* have proposed that shorter poly(A) tails are more actively translated, while longer tails are refractory to translation. Until recently, approaches for estimating poly(A) tail lengths were restricted to transcript-specific measurements that relied upon PCR and/or laborious Northern Blotting techniques. Such approaches suffer from low throughput, high workload and possible amplification artifacts. More recently, short-read sequencing strategies have been implemented to study poly(A) tail length in a transcriptome-wide manner. However, these approaches are technically restricted to a specific size of poly(A) tails depending upon sample enrichment and sequencing strategy. Moreover, most of these techniques rely upon PCR amplification of the poly(A) tail region, making them susceptible to amplification artefacts that affect poly(A) length measurements. Importantly, these techniques can only indirectly identify the transcript linked to the poly(A) by alignment of short sequences representing the RNA 3' ends, making it impossible in many cases to assign poly(A) tail measurements to specific transcript isoforms. The methods of the present disclosure address these and other shortcomings of existing approaches for determining the natural 3' ends of RNAs. Details regarding embodiments of the methods will now be described.

As summarized above, a polymer of the non-canonical nucleotides is added to the 3' end of the RNA by a polynucleotide-3' nucleotidyl transferase. By "polynucleotide-3' nucleotidyl transferase" is meant a nucleotidyl transferase enzyme capable of adding non-canonical nucleotides to the 3' end of an RNA, e.g., in a non-templated manner. A variety of suitable nucleotidyl transferases may be employed. In certain embodiments, the polynucleotide-3' nucleotidyl transferase is a uridylyltransferase, a cytidyltransferase, an adenyltransferase, a guanyltransferase, or a cytosyltransferase.

According to some embodiments, the polynucleotide-3' nucleotidyl transferase is a uridylyltransferase. In nature, RNA uridylylation plays a role in the biogenesis and metabolism of functional RNAs, and regulates cellular gene expression. RNA uridylylation is catalyzed by a subset of proteins from the non-canonical terminal nucleotidyltransferase family. A variety of suitable uridylyltransferases may be employed when practicing the methods of the present disclosure. In some embodiments, the uridylyltransferase is a mammalian uridylyltransferase. Non-limiting examples of mammalian uridylyltransferases include human uridylyltransferases such as terminal uridylyl transferase 1 (TUT1—UniProtKB AOAOS2Z5L2), terminal uridylyl transferase 4 (TUT4—UniProtKB Q5TAX3), terminal uridylyl transferase 7 (TUT7—UniProtKB Q5VYS8), and variants thereof capable of adding a polymer of non-canonical nucleotides to the 3' end of an RNA. According to some embodiments, the uridylyltransferase is a yeast uridylyltransferase. For example, the uridylyltransferase may be from a fission yeast. A non-limiting example of a fission yeast uridylyltransferase that may be employed is *Schizosaccharomyces pombe* cid1 (*S. pombe* cid1—UniProtKB—O13833) or a variant thereof capable of adding a polymer of non-canonical nucleotides to the 3' end of an RNA.

The polynucleotide-3' nucleotidyl transferase may be *Caenorhabditis elegans* MUT-2 or a variant thereof capable of adding a polymer of non-canonical nucleotides to the 3' end of an RNA. The polynucleotide-3' nucleotidyl transferase may be *Caenorhabditis elegans* *F*31C3.2 or a variant thereof capable of adding a polymer of non-canonical nucleotides to the 3' end of an RNA. According to some embodiments, the polynucleotide-3' nucleotidyl transferase is *C. elegans* PUP-1, PUP-2, PUP-3, F43E2.1, ZK863.4, GLD-2, GLD-4, C53A5.16, F43H9.3, or a variant thereof capable of adding a polymer of non-canonical nucleotides to the 3' end of an RNA. In certain embodiments, the polynucleotide-3' nucleotidyl transferase is *S. pombe* Cid1, Cid16, Cid11, Cid12, Cid13, Cid14, or a variant thereof capable of adding a polymer of non-canonical nucleotides to the 3' end of an RNA. According to some embodiments, the polynucleotide-3' nucleotidyl transferase is *S. cerevisiae* Trf4, Trf5, or a variant thereof capable of adding a polymer of non-canonical nucleotides to the 3' end of an RNA. In certain embodiments, the polynucleotide-3' nucleotidyl transferase is *N. crassa* NCU04364.7, TRF4, NCU00538.7, NCU11050.7, or a variant thereof capable of adding a polymer of non-canonical nucleotides to the 3' end of an RNA. According to some embodiments, the polynucleotide-3' nucleotidyl transferase is *A. nidulans* cutA, cutB, or a variant thereof capable of adding a polymer of non-canonical nucleotides to the 3' end of an RNA. In certain embodiments, the polynucleotide-3' nucleotidyl transferase is *H. sapiens* TUT4, TUT7, TUT1 (Star-PAP), TENT2 (GLD2), TENT4B (PAPD5), TENT4A, or a variant thereof capable of adding a polymer of non-canonical nucleotides to the 3' end of an RNA. According to some embodiments, the polynucleotide-3' nucleotidyl transferase is *C. albicans* Trf4, CR_03940 W_A, RPN1, or a variant thereof capable of adding a polymer of non-canonical nucleotides to the 3' end of an RNA. Information regarding the foregoing polynucleotide-3' nucleotidyl transferases may be found in Preston et al. (2019) Nature Methods 16:437-445, the disclosure of which is incorporated herein by reference in its entirety for all purposes.

In certain embodiments, the polynucleotide-3' nucleotidyl transferase is a variant of a wild-type polynucleotide-3' nucleotidyl transferase. By "variant" is meant a functional variant in which the enzyme retains its non-canonical nucleotide transferase activity and includes one or more amino acid substitutions, one or more amino acid insertions, and/or one or more amino acid deletions (e.g., one or more internal deletions and/or a C- and/or N-terminal truncation) as compared to the wild-type parental enzyme. Variants of interest include those that enhance the stability of the enzyme, those which expand the repertoire of non-canonical nucleotides which the enzyme is capable of adding to the 3' end of an RNA, those that enhance the yield of the enzyme when recombinantly expressed, and/or the like. In certain embodiments, a variant polynucleotide-3' nucleotidyl transferase has at least 70%, at least 75%, at least 80%, at least 85%, at least 90%, at least 95%, or at least 99% amino acid sequence identity to the corresponding wild-type polynucleotide-3' nucleotidyl transferase, while retaining non-canonical nucleotide transferase activity.

In certain embodiments, a variant of a wild-type polynucleotide-3' nucleotidyl transferase comprises one or more conservative amino acid substitutions. A "conservative substitution" is one in which an amino acid is substituted for another amino acid that has similar properties, such that one skilled in the art of peptide chemistry would expect the secondary structure and hydropathic nature of the enzyme to be substantially unchanged. When it is desired to alter the amino acid sequence of an enzyme to create an equivalent, or even an improved, variant enzyme, one skilled in the art, for example, can change one or more of the codons of the encoding DNA sequence.

According to some embodiments, the polynucleotide-3' nucleotidyl transferase comprises an N-terminal truncation. By "N-terminal truncation" is meant one or more amino acids are absent from the N-terminal end of the polynucleotide-3' nucleotidyl transferase as compared to the corresponding wild-type polynucleotide-3' nucleotidyl transferase. In some instances, an N-terminal truncation finds use in enhancing the stability of the polynucleotide-3' nucleotidyl transferase, e.g., a uridylyltransferase. For example, it has been found that an N-terminally truncated form of *S. pombe* cid1 uridylyltransferase exhibits greater stability than full-length *S. pombe* cid1. See Rissland et al. (2007) *Molecular and Cellular Biology* 27(10):3612-3624. In some embodiments, the polynucleotide-3' nucleotidyl transferase is a uridylyltransferase (e.g., *S. pombe* cid1) comprising an N-terminal truncation of from 5 to 60 amino acids, such as from 10 to 50, from 20 to 40 amino acids, from 30 to 40 amino acids, or from 35 to 40 amino acids. In one non-limiting example, such a uridylyltransferase is an N-terminally truncated *S. pombe* cid1 that includes a 35-40 amino acid (e.g., 37 amino acid) N-terminal truncation. The non-truncated portion of such an enzyme may have 100% amino acid sequence identity to the corresponding portion of wild-type *S. pombe* cid1 (SEQ ID NO:1). In certain embodiments, the non-truncated portion of such an enzyme has at least 70%, at least 75%, at least 80%, at least 85%, at least 90%, at least 95%, or at least 99% amino acid sequence identity to the corresponding portion of wild-type *S. pombe* cid1 (SEQ ID NO:1), while retaining non-canonical nucleotide transferase activity.

According to some embodiments, the polynucleotide-3' nucleotidyl transferase is part of a fusion protein comprising the polynucleotide-3' nucleotidyl transferase and a heterologous sequence of amino acids. Heterologous amino acid sequences of interest include those that enhance the stability of the enzyme, facilitate purification of enzyme (e.g., after recombinant expression of the enzyme in a host cell), and/or provide any other useful feature to the enzyme. In certain embodiments, the heterologous sequence of amino acids comprises a purification tag. Non-limiting examples of a purification tag that may be provided by the heterologous sequence of amino acids include a FLAG tag (DYKDDDDK (SEQ ID NO:4)), an HA tag (YPYDVPDYA (SEQ ID NO:5)), a His tag (e.g., including from 5-10 histidines, e.g., a His10 tag (HHHHHHHHHH (SEQ ID NO:6))), a Myc tag (EQKLISEEDL (SEQ ID NO:7)), and/or any other convenient purification tag.

According to some embodiments, when the polynucleotide-3' nucleotidyl transferase is part of a fusion protein, the heterologous sequence of amino acids is from 2 to 75, 3 to 50, 4 to 40, or from 5 to 30 amino acids in length, e.g., 20-25 amino acids in length. In certain embodiments, the heterologous sequence is N-terminal to the polynucleotide-3' nucleotidyl transferase portion of the fusion protein. According to some embodiments, the heterologous sequence is C-terminal to the polynucleotide-3' nucleotidyl transferase portion of the fusion protein. In some embodiments, the fusion protein comprises a first heterologous sequence N-terminal to the polynucleotide-3' nucleotidyl transferase portion and a second heterologous sequence C-terminal to the polynucleotide-3' nucleotidyl transferase portion of the fusion protein.

In certain embodiments, the heterologous sequence includes a protease cleavage site that facilitates removal of all or a portion of the heterologous sequence from the polynucleotide-3' nucleotidyl transferase portion of the fusion protein. By way of example, when the heterologous sequence includes a purification tag, the heterologous sequence may include a protease cleavage site disposed between the purification tag and the polynucleotide-3' nucleotidyl transferase portion of the fusion protein, e.g., when it is desirable to remove the purification tag prior to employing the polynucleotide-3' nucleotidyl transferase portion in the methods of the present disclosure. Any convenient protease cleavage site may be provided. In one non-limiting example, the protease cleavage site is a cleavage site for Tobacco Etch Virus (TEV) protease. The recognition site for TEV protease is ENLYFQS (SEQ ID NO:8), where the scissile bond is between the Q and S. According to some embodiments, when the heterologous sequence comprises a protease cleavage site, the protease cleavage site is within 10, 9, 8, 7, 6, 5, 4, 3, or 2 amino acids (e.g., within 1 amino acid) of the polynucleotide-3' nucleotidyl transferase portion of the fusion protein.

The amino acid sequences of full-length wild-type *S. pombe* cid1 (SEQ ID NO:1) and a variant *S. pombe* cid1 (SEQ ID NO:2—sometimes referred to herein as "vCID") that includes a 37 amino acid N-terminal truncation and N-terminal heterologous sequence (bold) that includes a His10 purification tag (italicized) and TEV protease cleavage site (underlined) are provided in Table 1. Also provided in Table 1 is the nucleic acid sequence (SEQ ID NO:3) of a plasmid that includes a coding region for the variant *S. pombe* cid1.

TABLE 1

Amino acid and nucleotide sequences for example *S. pombe* cid1 uridylyltransferases

| | |
|---|---|
| S. pombe cid1-<br>(UniProtKB-<br>O13833)<br>SEQ ID NO: 1 | MNISSAQFIPGVHTVEEIEAEIHKNLHISKSCSYQKVPNSHKEFTKFCYEVYNEIKIS<br>DKEFKEKRAALDTLRLCLKRISPDAELVAFGSLESGLALKNSDMDLCVLMDSRVQS<br>DTIALQFYEELIAEGFEGKFLQRARIPIIKLTSDTKNGFGASFQCDIGFNNRLAIHNTL<br>LLSSYTKLDARLKPMVLLVKHWAKRKQINSPYFGTLSSYGYVLMVLYYLIHVIKPPV<br>FPNLLLSPLKQEKIVDGFDVGFDDKLEDIPPSQNYSSLGSLLHGFFRFYAYKFEPR<br>EKVVTFRRPDGYLTKQEKGWTSATEHTGSADQIIKDRYILAIEDPFEISHNVGRTVS<br>SSGLYRIRGEFMAASRLLNSRSYPIPYDSLFEEAPIPPRRQKKTDEQSNKKLLNET<br>DGDNSE |
| S. pombe cid1<br>37 amino acid N-<br>terminal<br>truncation<br>HIS10 tag<br>TEV protease<br>cleavage site<br>SEQ ID NO: 2 | **MG*HHHHHHHHHH*SSGAENLYFQS**PNSHKEFTKFCYEVYNEIKISDKEFKEKRAAL<br>DTLRLCLKRISPDAELVAFGSLESGLALKNSDMDLCVLMDSRVQSDTIALQFYEELI<br>AEGFEGKFLQRARIPIIKLTSDTKNGFGASFQCDIGFNNRLAIHNTLLLSSYTKLDAR<br>LKPMVLLVKHWAKRKQINSPYFGTLSSYGYVLMVLYYLIHVIKPPVFPNLLLSPLKQ<br>EKIVDGFDVGFDDKLEDIPPSQNYSSLGSLLHGFFRFYAYKFEPREKVVTFRRPDG<br>YLTKQEKGWTSATEHTGSADQIIKDRYILAIEDPFEISHNVGRTVSSSGLYRIRGEF<br>MAASRLLNSRSYPIPYDSLFEEAPIPPRRQKKTDEQSNKKLLNETDGDNSE |
| Plasmid 10H-<br>tev-vCID<br>SEQ ID NO: 3 | TCGCGCGTTTCGGTGATGACGGTGAAAACCTCTGACACATGCAGCTCCCGGA<br>GACGGTCACAGCTTGTCTGTAAGCGGATGCCGGGAGCAGACAAGCCCGTCAG<br>GGCGCGTCAGCGGGTGTTGGCGGGTGTCGGGGCTGGCTTAACTATGCGGCA<br>TCAGAGCAGATTGTACTGAGAGTGCACCAAATGCGGTGTGAAATACCGCACAG<br>ATGCGTAAGGAGAAAATACCGCATCAGGCGCCATTCGCCATTCAGGCTGCGC<br>AACTGTTGGGAAGGGCGATCGGTGCGGGCCTCATCGCTATTACGCCAGCTGG<br>CGAAAGGGGGATGTGCTGCAAGGCGATTAAGTTGGGTAACGCCAGGGTTTTC<br>CCAGTCACGACGTTGTAAAACGACGGCCAGTGCAACGCGATGACGATGGATA<br>GCGATTCATCGATGAGCTGACCCGATCGCCGCCGCCGGAGGGTTGCGTTTGA<br>GACGGGCGACAGATAGATCTGACGATAGTCATGCCCCGCGCCCACCGGAAG<br>GAGCTGACTGGGTTGAAGGCTCTCAAGGGCATCGGTCGAGATCCCGGTGCCT<br>AATGAGTGAGCTAACTTACATTAATTGCGTTGCGCTCACTGCCCGCTTTCCAGT<br>CGGGAAACCTGTCGTGCCAGCTGCATTAATGAATCGGCCAACGCGCGGGGAG<br>AGGCGGTTTGCGTATTGGGCGCCAGGGTGGTTTTTCTTTTCACCAGTGAGACG<br>GGCAACAGCTGATTGCCCTTCACCGCCTGGCCCTGAGAGAGTTGCAGCAAGC<br>GGTCCACGCTGGTTTGCCCCAGCAGGCGAAAATCCTGTTTGATGGTGGTTAAC<br>GGCGGGATATAACATGAGCTGTCTTCGGTATCGTCGTATCCCACTACCGAGAT<br>ATCCGCACCAACGCGCAGCCCGGACTCGGTAATGGCGCGCATTGCGCCCAG<br>CGCCATCTGATCGTTGGCAACCAGCATCGCAGTGGGAACGATGCCCTCATTC<br>AGCATTTGCATGGTTTGTTGAAAACCGGACATGGCACTCCAGTCGCCTTCCCG<br>TTCCGCTATCGGCTGAATTTGATTGCGAGTGAGATATTTATGCCAGCCAGCCA<br>GACGCAGACGCGCCGAGACAGAACTTAATGGGCCCGCTAACAGCGCGATTTG<br>CTGGTGACCCAATGCGACCAGATGCTCCACGCCCAGTCGCGTACCGTCTTCA<br>TGGGAGAAAATAATACTGTTGATGGGTGTCTGGTCAGAGACATCAAGAAATAA<br>CGCCGGAACATTAGTGCAGGCAGCTTCCACAGCAATGGCATCCTGGTCATCC<br>AGCGGATAGTTAATGATTAGCCCACTGACGCGTTGCGCGAGAAGATTGTGCAC<br>CGCCGCTTTACAGGCTTCGACGCCGCTTCGTTCTACCATCGACACCACCACG<br>CTGGCACCCAGTTGATCGGCGCGAGATTTAATCGCCGCGACAATTTGCGACG<br>GCGCGTGCAGGGCCAGACTGGAGGTGGCAACGCCAATCAGCAACGACTGTTT<br>GCCCGCCAGTTGTTGTGCCACGCGGTTGGGAATGTAATTCAGCTCCGCCATC<br>GCCGCTTCCACTTTTTCCCGCGTTTTCGCAGAAACGTGGCTGGCCTGGTTCAC<br>CACGCGGGAAACGGTCTGATAAGAGACACCGGCATACTCTGCGACATCGTAT<br>AACGTTACTGGTTTCACATTCACCACCCTGAATTGACTCTCTTCCGGGCGCTAT<br>CATGCCATACCGCGAAAGGTTTTGCGCCATTCGATGGTGTCCGGGATCTCGA<br>CGCTCTCCCTTATGCGACTCCTGCATTAGGAAGCAGCCCAGTAGTAGGTTGAG<br>GCCGTTGAGCACCGCCGCCGCAAGGAATGGTGCATGCAAGGAGATGGCGCC<br>CAACAGTCCCCCGGCCACGGGGCCTGCCACCATACCCACGCCGAAACAAGC<br>GCTCATGAGCCCGAAGTGGCGAGCCCGATCTTCCCCATCGGTGATGTCGGCG<br>ATATAGGCGCCAGCAACCGCACCTGTGGCGCCGGTGATGCCGGCCACGATG<br>CGTCCGGCGTAGAGGATCGAGATCTCGATCCCGCGAAATTAATACGACTCACT<br>ATAGGGGAATTGTGAGCGGATAACAATTCCCCTCTAGAAATAATTTTGTTTAAC<br>TTTAAGAAGGAGATATACCATGGGCCATCACCACCATCATCACCATCACCATC |

TABLE 1-continued

Amino acid and nucleotide sequences for example *S. pombe* cid1 uridylyltransferases

```
ACAGCAGCGGCGCGGAAAACCTGTATTTTCAGAGCCCGAACAGCCATAAAGA
ATTTACCAAATTTTGCTATGAAGTGTATAACGAAATTAAAATTAGCGATAAAGAA
TTTAAAGAAAAACGCGCGGCGCTGGATACCCTGCGCCTGTGCCTGAAACGCA
TTAGCCCGGATGCGGAACTGGTGGCGTTTGGCAGCCTGGAAAGCGGCCTGG
CGCTGAAAAACAGCGATATGGATCTGTGCGTGCTGATGGATAGCCGCGTGCA
GAGCGATACCATTGCGCTGCAGTTTTATGAAGAACTGATTGCGGAAGGCTTTG
AAGGCAAATTTCTGCAGCGCGCGCGCATTCCGATTATTAAACTGACCAGCGAT
ACCAAAAACGGCTTTGGCGCGAGCTTTCAGTGCGATATTGGCTTTAACAACCG
CCTGGCGATTCATAACACCCTGCTGCTGAGCAGCTATACCAAACTGGATGCGC
GCCTGAAACCGATGGTGCTGCTGGTGAAACATTGGGCGAAACGCAAACAGAT
TAACAGCCCGTATTTTGGCACCCTGAGCAGCTATGGCTATGTGCTGATGGTGC
TGTATTATCTGATTCATGTGATTAAACCGCCGGTGTTTCCGAACCTGCTCCTGA
GCCCGCTGAAACAGGAAAAAATTGTGGATGGCTTTGATGTGGGCTTTGATGAT
AAACTGGAAGATATTCCGCCGAGCCAGAACTATAGCAGCCTGGGCAGCCTGC
TGCATGGCTTTTTTCGCTTTTATGCGTATAAATTTGAACCGCGCGAAAAAGTGG
TGACCTTTCGCCGCCCGGATGGCTATCTGACCAAACAGGAAAAAGGCTGGAC
CAGCGCGACCGAACATACCGGCAGCGCGGATCAGATTATTAAAGATCGCTATA
TTCTGGCGATTGAAGATCCGTTTGAAATTAGCCATAACGTGGGCGCACCGTG
AGCAGCAGCGGCCTGTATCGCATTCGCGGCGAATTTATGGCGGCGAGCCGCC
TGCTGAACAGCCGCAGCTATCCGATTCCGTATGATAGCCTGTTTGAAGAAGCG
CCGATTCCGCCGCGCCGCCAGAAAAAAACCGATGAACAGAGCAACAAAAAAC
TGCTGAACGAAACCGATGGCGATAACAGCGAATAAGGATCCGGCTGCTAACA
AAGCCCGAAAGGAAGCTGAGTTGGCTGCTGCCACCGCTGAGCAATAACTAGC
ATAACCCCTTGGGGCCTCTAAACGGGTCTTGAGGGGTTTTTTGCTGAAAGGAT
CAGTTCTGGACCAGCGAGCTGTGCTGCGACTCGTGGCGTAATCATGGTCATA
GCTGTTTCCTGTGTGAAATTGTTATCCGCTCACAATTCCACACAACATACGAGC
CGGAAGCATAAAGTGTAAAGCCTGGGGTGCCTAATGAGTGAGCTAACTCACAT
TAATTGCGTTGCGCTCACTGCCCGCTTTCCAGTCGGGAAACCTGTCGTGCCAG
CTGCATTAATGAATCGGCCAACGCGCGGGGAGAGGCGGTTTGCGTATTGGGC
GCTCTTCCGCTTCCTCGCTCACTGACTCGCTGCGCTCGGTCGTTCGGCTGCG
GCGAGCGGTATCAGCTCACTCAAAGGCGGTAATACGGTTATCCACAGAATCAG
GGGATAACGCAGGAAAGAACATGTGAGCAAAAGGCCAGCAAAAGGCCAGGAA
CCGTAAAAAGGCCGCGTTGCTGGCGTTTTTCCATAGGCTCCGCCCCCCTGAC
GAGCATCACAAAAATCGACGCTCAAGTCAGAGGTGGCGAAACCCGACAGGAC
TATAAAGATACCAGGCGTTTCCCCCTGGAAGCTCCCTCGTGCGCTCTCCTGTT
CCGACCCTGTCGCTTACCGGATACCTGTCCGCCTTTCTCCCTTCGGGAAGCGT
GGCGCTTTCTCATAGCTCACGCTGTAGGTATCTCAGTTCGGTGTAGGTCGTTC
GCTCCAAGCTGGGCTGTGTGCACGAACCCCCCGTTCAGCCCGACCGCTGCG
CCTTATCCGGTAACTATCGTCTTGAGTCCAACCCGGTAAGACACGACTTATCG
CCACTGGCAGCAGCCACTGGTAACAGGATTAGCAGAGCGAGGTATGTAGGCG
GTGCTACAGAGTTCTTGAAGTGGTGGCCTAACTACGGCTACACTAGAAGAACA
GTATTTGGTATCTGCGCTCTGCTGAAGCCAGTTACCTTCGGAAAAAGAGTTGG
TAGCTCTTGATCCGGCAAACAAACCACCGCTGGTAGCGGTGGTTTTTTTGTTT
GCAAGCAGCAGATTACGCGCAGAAAAAAAGGATCTCAAGAAGATCCTTTGATC
TTTTCTACGGGGTCTGACGCTCAGTGGAACGAAAACTCACGTTAAGGGATTTT
GGTCATGAGATTATCAAAAAGGATCTTCACCTAGATCCTTTTAAATTAAAAATGA
AGTTTTAAATCAATCTAAAGTATATATGAGTAAACTTGGTCTGACAGTTACCAAT
GCTTAATCAGTGAGGCACCTATCTCAGCGATCTGTCTATTTCGTTCATCCATAG
TTGCCTGACTCCCCGTCGTGTAGATAACTACGATACGGGAGGGCTTACCATCT
GGCCCCAGTGCTGCAATGATACCGCGAGACCCACGCTCACCGGCTCCAGATT
TATCAGCAATAAACCAGCCAGCCGGAAGGGCCGAGCGCAGAAGTGGTCCTGC
AACTTTATCCGCCTCCATCCAGTCTATTAATTGTTGCCGGGAAGCTAGAGTAAG
TAGTTCGCCAGTTAATAGTTTGCGCAACGTTGTTGCCATTGCTACAGGCATCG
TGGTGTCACGCTCGTCGTTTGGTATGGCTTCATTCAGCTCCGGTTCCCAACGA
TCAAGGCGAGTTACATGATCCCCATGTTGTGCAAAAAAGCGGTTAGCTCCTT
CGGTCCTCCGATCGTTGTCAGAAGTAAGTTGGCCGCAGTGTTATCACTCATGG
TTATGGCAGCACTGCATAATTCTCTTACTGTCATGCCATCCGTAAGATGCTTTT
CTGTGACTGGTGAGTACTCAACCAAGTCATTCTGAGAATAGTGTATGCGGCGA
CCGAGTTGCTCTTGCCCGGCGTCAATACGGGATAATACCGCGCCACATAGCA
GAACTTTAAAAGTGCTCATCATTGGAAAACGTTCTTCGGGGCGAAAACTCTCAA
GGATCTTACCGCTGTTGAGATCCAGTTCGATGTAACCCACTCGTGCACCCAAC
TGATCTTCAGCATCTTTTACTTTCACCAGCGTTTCTGGGTGAGCAAAAACAGGA
AGGCAAAATGCCGCAAAAAAGGGAATAAGGGCGACACGGAAATGTTGAATACT
CATACTCTACCTTTTCAATATTATTGAAGCATTTATCAGGGTTATTGTCTCATG
AGCGGATACATATTTGAATGTATTTAGAAAAATAAACAAATAGGGGTTCCGCGC
ACATTTCCCCGAAAAGTGCCACCTGACGTCTAAGAAACCATTATTATCATGACA
TTAACCTATAAAAATAGGCGTATCACGAGGCCCTTTCGTC
```

The polynucleotide-3' nucleotidyl transferase or fusion protein comprising same may be produced using a variety of techniques. In certain embodiments, the polynucleotide-3' nucleotidyl transferase is produced by transforming, transfecting, or transducing a host cell with a nucleic acid that encodes the polynucleotide-3' nucleotidyl transferase or fusion protein. By "transform" or "transfect" is meant the uptake of foreign DNA by a cell. A cell has been "transformed" or "transfected" when exogenous DNA has been introduced inside the cell wall or cell membrane. A number of transfection techniques are generally known in the art. See, e.g., Sambrook et al. (2001) Molecular Cloning, a laboratory manual, 3rd edition, Cold Spring Harbor Laboratories, New York, Davis et al. (1995) Basic Methods in Molecular Biology, 2nd edition, McGraw-Hill, and Chu et al. (1981) Gene 13:197. Such techniques can be used to introduce one or more exogenous DNA moieties into suitable host cells. The term refers to both stable and transient uptake of the genetic material.

Once the host cell includes the nucleic acid encoding the polynucleotide-3' nucleotidyl transferase or fusion protein (e.g., present in a suitable expression vector), the polynucleotide-3' nucleotidyl transferase or fusion protein may be produced by culturing the cell under conditions in which the polynucleotide-3' nucleotidyl transferase or fusion protein is expressed. Such conditions for prokaryotic and eukaryotic cells are known by those of skill in the art. A non-limiting example of such conditions for producing a polynucleotide-3' nucleotidyl transferase or fusion protein in *E. coli* is provided in the Experimental section below. In eukaryotic cells, such conditions typically include culturing the cell in a suitable container (e.g., a cell culture plate or well thereof), in a suitable medium (e.g., cell culture medium, such as DMEM, RPMI, MEM, IMDM, DMEM/F-12, or the like) at a suitable temperature (e.g., 32° C.-42° C., such as 37° C.) and pH (e.g., pH 7.0-7.7, such as pH 7.4) in an environment having a suitable percentage of $CO_2$, e.g., 3% to 10%, such as 5%).

Upon expression of the polynucleotide-3' nucleotidyl transferase or fusion protein in a host cell, it may be desirable or necessary to purify the polynucleotide-3' nucleotidyl transferase or fusion protein prior to use for adding a polymer of non-canonical nucleotides to the 3' end of the RNA. For example, when the polynucleotide-3' nucleotidyl transferase is part of a fusion protein comprising a heterologous sequence comprising a purification tag, the fusion protein may be purified using an approach appropriate for the particular purification tag. For example, when a His tag is employed, the fusion protein may be purified using the example purification strategy described in Example 1 below.

A summarized above, the methods include combining non-canonical nucleotides into the reaction mixture. As used herein, a "non-canonical nucleotide" is any nucleotide other than rATP, rCTP, rGTP and rUTP. A non-canonical nucleotide may be a naturally occurring nucleotide (e.g., a thymine-containing nucleotide) or may be non-naturally occurring, e.g., a non-naturally occurring nucleotide analog, etc. Non-limiting examples of non-canonical nucleotides that find use in practicing the methods of the present disclosure include inosine, 5-methyluracil (ribothymidine), 4-thiouracil, 6-methyladenine, 2'-O-methyladenine, and any combination thereof.

According to some embodiments, a homopolymer of non-canonical nucleotides is added to the 3' end of the RNA. For example, a homopolymer of inosine, 5-methyluracil (ribothymidine), 4-thiouracil, 6-methyladenine, or 2'-O-methyladenine may be added to the 3' end of the RNA. In certain embodiments, a heteropolymer of non-canonical nucleotides is added to the 3' end of the RNA. According to some embodiments, when a heteropolymer of non-canonical nucleotides is added to the 3' end of the RNA, the heteropolymer includes inosines and one or more non-inosine non-canonical nucleotides. In certain embodiments, when a heteropolymer of non-canonical nucleotides is added to the 3' end of the RNA, the heteropolymer includes two or more types of non-canonical nucleotides selected from inosines, 5-methyluracil (ribothymidine), 4-thiouracil, 6-methyladenine, 2'-O-methyladenine, and any combination thereof.

According to the present methods, a polymer of non-canonical nucleotides is added to the 3' end of an RNA. The RNA may be from any RNA sample of interest. The RNA sample of interest may be isolated from a single cell, a plurality of cells (e.g., cultured cells), a tissue, an organ, or an organism (e.g., bacteria, yeast, or the like). In certain aspects, the RNA sample of interest is isolated from a cell(s), tissue, organ, and/or the like of an animal. In some embodiments, the animal is a mammal (e.g., a mammal from the genus Homo (e.g., a human), a rodent (e.g., a mouse or rat), a dog, a cat, a horse, a cow, or any other mammal of interest). In other aspects, the RNA sample is isolated/obtained from a source other than a mammal, such as bacteria, yeast, insects (e.g., *drosophila*), amphibians (e.g., frogs (e.g., *Xenopus*)), viruses, plants, or any other non-mammalian nucleic acid sample source.

In certain embodiments, the RNA is from a biological fluid sample (e.g., blood, saliva, a bone marrow suspension, cerebrospinal fluid, gastric fluid, synovial fluid, urine, lymph, semen, seminal fluid, mucus, tears, sweat, amniotic fluid or the like), a tissue sample (e.g., a tissue sample from brain, lung, breast, skin, heart, colon, pancreas, prostate, ovary, testis, cardiac muscle, skeletal muscle, adipose tissue, or the like) or a cell culture. According to some embodiments, the RNA is isolated from a disease-free cell or a diseased cell. By "diseased" is meant any condition or disorder that damages or interferes with the normal function of a cell, tissue, or organ. In certain aspects, when the RNA is isolated from a diseased cell (e.g., a diseased human cell), the cell is a tumor cell. As used herein, a "tumor cell" or "cancer cell" is a cell which exhibits abnormal changes in proliferation, cell death, cell metabolism, cell signaling, immune response, replicative control, and/or motility due to environmental, genetic or epigenetic factors. The tumor cell may be derived from cancers of the colon, breast, lung, prostate, skin, pancreas, brain, kidney, endometrium, cervix, ovary, thyroid, or other glandular tissue carcinomas or melanoma, lymphoma, or any other cancers of interest. In some embodiments, the RNA is from a circulating tumor cell (CTC).

Approaches, reagents and kits for isolating RNA from sources of interest are known in the art and commercially available. For example, kits for isolating RNA from a source of interest include the RNeasy®, QIAamp®, QIAprep® and QIAquick® nucleic acid isolation/purification kits by Qiagen, Inc. (Germantown, Md); the ChargeSwitch®, Purelink®, GeneCatcher® nucleic acid isolation/purification kits by Life Technologies, Inc. (Carlsbad, CA); the NucleoMag®, NucleoSpin®, and NucleoBond® nucleic acid isolation/purification kits by Clontech Laboratories, Inc. (Mountain View, CA), and TRIzol™ reagent by Invitrogen™. In certain aspects, the RNA is isolated from a fixed biological sample, e.g., formalin-fixed, paraffin-embedded (FFPE) tissue. RNA from FFPE tissue may be isolated using commercially available kits—such as the AllPrep@ DNA/RNA FFPE kit by Qiagen, Inc. (Germantown, Md), the RecoverAll® Total Nucleic Acid Isolation kit for FFPE by Life Technologies, Inc. (Carlsbad, CA), and the NucleoSpin® FFPE kits by Clontech Laboratories, Inc. (Mountain View, CA).

In certain embodiments, the RNA to which the polymer of non-canonical nucleotides is added is a polyadenylated RNA. For example, the RNA may be a eukaryotic RNA. According to some embodiments, the RNA to which the polymer of non-canonical nucleotides is added is non-polyadenylated RNA. For example, the RNA may be a ribosomal RNA. The RNA may be any type of RNA (or sub-type thereof) including, but not limited to, a messenger RNA (mRNA), a microRNA (miRNA), a small interfering RNA (siRNA), a transacting small interfering RNA (ta-siRNA), a natural small interfering RNA (nat-siRNA), a ribosomal RNA (rRNA), a transfer RNA (tRNA), a small nucleolar RNA (snoRNA), a small nuclear RNA (snRNA), a long non-coding RNA (lncRNA), a non-coding RNA (ncRNA), a transfer-messenger RNA (tmRNA), a precursor messenger RNA (pre-mRNA), a small Cajal body-specific RNA (scaRNA), a piwi-interacting RNA (piRNA), an endoribonuclease-prepared siRNA (esiRNA), a small temporal RNA (stRNA), a signal recognition RNA, a telomere RNA, a ribozyme, or the like.

The RNA, polynucleotide-3' nucleotidyl transferase and non-canonical nucleotides are combined in a reaction mixture under conditions in which the polynucleotide-3' nucleotidyl transferase adds a polymer of the non-canonical nucleotides to the 3' end of the RNA. Such reaction conditions may vary depending upon the polynucleotide-3' nucleotidyl transferase employed, the type of non-canonical nucleotides employed, and/or the like. Such reaction conditions will typically include the selection of a suitable buffer, metal cofactor for enzyme activity (if required), salts, concentrations thereof, pH, temperature, and/or the like, which may be determined by those of ordinary skill in the field of molecular biology without undue experimentation. Detailed example reaction conditions for using an *S. pombe* cid1 uridylyltransferase to add a polymer of non-canonical nucleotides to the 3' ends of RNAs are provided in Example 2 below, which reaction conditions are suitable for a wide variety of polynucleotide-3' nucleotidyl transferases.

The reaction conditions may be selected to produce polymers of non-canonical nucleotides of a desired length. Conditions that may be selected to produce polymers of the desired length include, e.g., the duration of the reaction, the concentration of the polynucleotide-3' nucleotidyl transferase, the concentration of the non-canonical nucleotides, the temperature of the reaction, the concentration of a metal cofactor for the polynucleotide-3' nucleotidyl transferase, and/or the like. In some embodiments, the conditions are such that—on average—from 5 to 500 (e.g., from 5 to 100) non-canonical nucleotides are added to the 3' ends of RNAs in the sample, e.g., from 5 to 400, 10 to 300, 20 to 200, 30 to 100, or 40 to 75 (e.g., from 45 to 55) non-canonical nucleotides are added to the 3' end of the RNA on average. According to some embodiments, on average, more than 10 but 200 or fewer, 150 or fewer, 100 or fewer, 90 or fewer, 80 or fewer, 70 or fewer, 60 or fewer, or 50 or fewer non-canonical nucleotides are added to the 3' end of the RNA.

In certain embodiments, upon addition of the polymer of non-canonical nucleotides to the 3' end of the RNA, the methods may further include analyzing the RNA, e.g., using an analysis method that exploits the polymer of non-canonical nucleotides added to the 3' end of the RNA. According to some embodiments, the methods further include analyzing the RNA using a nanopore. In some embodiments, when the methods further include analyzing the RNA using a nanopore, the methods include translocating the RNA and added polymer through or adjacent a nanopore of a nanopore device, wherein the nanopore devices comprises a thin film separating a cis compartment from a trans compartment, the thin film comprising the nanopore therein. Such methods may further include monitoring ionic current through the nanopore during the translocating. The rate of translocation may be controlled to permit discrimination of individual nucleotides or "blocks" of nucleotide sequences of the RNA and polymer of non-canonical nucleotides based on changes in the ionic current.

As will be appreciated with the benefit of the present disclosure, in certain embodiments, the polymer of non-canonical nucleotides added to the 3' end of the RNA may facilitate nanopore-based identification of the 3' end of the RNA. For example, the non-canonical nucleotides may be selected such that the polymer of non-canonical nucleotides added to the 3' end of the RNA when translocating through or adjacent the nanopore results in an ionic current through the nanopore that is readily distinguishable from the ionic current through the nanopore when the RNA portion of the molecule (which may include a poly(A) portion of the RNA in the case of a polyadenylated RNA) is translocating through or adjacent the nanopore. In the non-limiting example of a homopolymer of inosines, such a distinguishable current is demonstrated in Example 3 below and FIG. 4.

Accordingly, in certain embodiments, the methods include identifying the polymer of non-canonical nucleotides added to the 3' end of the RNA using a nanopore. Such methods may further include determining the junction between the 3' end of the RNA and the polymer of non-canonical nucleotides to identify the 3' end of the RNA. According to some embodiments, the nanopore-based analysis includes sequencing the RNA or a portion thereof, e.g., the complete RNA or a 3' portion of the RNA.

Any nanopore device suitable for translocating the RNA and added polymer through or adjacent a nanopore and monitoring ionic current through the nanopore may be employed when practicing the subject methods. For example, a suitable device may include a chamber including an aqueous solution and a thin film that separates the chamber into two sections, the membrane including a nanopore formed therein. Electrical measurements may be made using single channel recording equipment such as that described, e.g., in Lieberman et al. (2010) *J. Am. Chem. Soc.* 132(50):17961-72; Stoddart et al. (2009) *PNAS* 106(19): 7702-7; U.S. Pat. No. 9,481,908; and U.S. Patent Application Publication No. US2014/0051068; the disclosures of which are incorporated herein by reference in their entireties for all purposes. Alternatively, electrical measurements may be made using a multi-channel system, for example as described in U.S. Patent Application Publication No. US2015346149, the disclosure of which is incorporated herein by reference in its entirety for all purposes.

In nanopore-based analysis (e.g., sequencing), the nanopore serves as a biosensor and provides the sole passage through which an ionic solution on the cis side of the membrane contacts the ionic solution on the trans side. A constant voltage bias (trans side positive) produces an ionic current through the nanopore and drives ssDNA or ssRNA in the cis chamber through the pore to the trans chamber. A processive enzyme (e.g., a helicase, polymerase, nuclease, or the like) may be bound to the polynucleotide such that its step-wise movement controls and ratchets the nucleotides through the small-diameter nanopore, nucleobase by nucleobase. Because the ionic conductivity through the nanopore is sensitive to the presence of the nucleobase's mass and its associated electrical field, the ionic current levels through the nanopore reveal the sequence of nucleobases in the translocating strand. A patch clamp, a voltage clamp, or the like, may be employed.

Suitable conditions for measuring ionic currents through transmembrane pores (e.g., protein pores, solid state pores, etc.) are known in the art. Typically, a voltage is applied across the membrane and pore. The voltage used may be from +2 V to −2 V, e.g., from −400 mV to +400 mV. The voltage used may be in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage may be in the range of from 100 mV to 240 mV, e.g., from 120 mV to 220 mV.

The methods are typically carried out in the presence of a suitable charge carrier, such as metal salts, for example alkali metal salts, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. Generally, the salt is present in the aqueous solution in the chamber. Potassium chloride (KCl), sodium chloride (NaCl) or cesium chloride (CsCl) may be used, for example. The salt concentration may be at saturation. The salt concentration may be 3M or lower and is typically from 0.1 to 2.5 M, from 0.3 to 1.9 M, from 0.5 to 1.8 M, from 0.7 to 1.7 M, from 0.9 to 1.6 M, or from 1 M to 1.4 M. The salt concentration may be from 150 mM to 1 M. The methods are preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

In some embodiments, the rate of translocation is controlled using a processive enzyme (also referred to herein as a "motor protein"). Non-limiting examples of processive enzymes that may be employed include polymerases (e.g., a phi29 polymerase, a reverse transcriptase, or other suitable polymerase) and helicases, e.g., a Hel308 helicase, a RecD helicase, a TraI helicase, a TraI subgroup helicase, an XPD helicase, or the like. The RNA or polymer added thereto may be bound by the processive enzyme (e.g., by binding of the processive enzyme to a recognition site present in a sequencing adapter located at the 3' end of the polymer added to the RNA), followed by the resulting complex being drawn to the nanopore, e.g., by a potential difference applied across the nanopore. In other aspects, the processive enzyme may be located at the nanopore (e.g., attached to or adjacent to the nanopore) such that the processive enzyme binds the 3' end of the adapted polymer upon arrival of the adapted polymer at the nanopore.

The thin film may be a solid-state film, a biological membrane, or the like. In some embodiments, the nanopore is a solid-state nanopore. In other embodiments, the nanopore is a biological nanopore. The biological nanopore may be, e.g., an alpha-hemolysin-based nanopore, a *Mycobacterium smegmatis* porin A (MspA)-based nanopore, or the like.

Nanopore devices and methods that may be employed when practicing the methods of the present disclosure include those described in U.S. Patent Application Publication Nos. US2018/0087101, US2018/0037874, US2018/0030530, US2017/0363577, US2017/0335384, US2017/0326550, US2017/0283470, US2017/0253923, US2017/0253910, US2017/0204457, US2017/0107569, US2017/0067101, US2017/0058338, US2017/0091427, US2017/0022557, US2017/0002406, US2016/0251710, US2016/0010147, US2015/0344944, US2015/0268256, and US2015/0197796, the disclosures of which are herein incorporated by reference in their entireties for all purposes.

Details regarding nanopore-based polynucleotide sequencing are described, e.g., in Feng et al. (2015) Genomics, Proteomics & Bioinformatics 13(1):4-16. In some embodiments, the methods of the present disclosure employ a MinION™, GridIONx5™, PromethION™, or SmidgION™ nanopore device, available from Oxford Nanopore Technologies. Detailed design considerations and protocols for carrying out nanopore-based analysis and sequencing are provided with such systems.

Kits

As summarized above, aspects of the present disclosure also include kits. In certain embodiments, the kits find use in practicing the methods of the present disclosure. The kits, therefore, find use in a variety of applications, including research and clinical applications in which it is useful to add a polymer of non-canonical nucleotides to the 3' ends of RNAs, e.g., to determine the natural 3' ends of such RNAs, e.g., using a nanopore.

According to some embodiments, a kit of the present disclosure includes a polynucleotide-3' nucleotidyl transferase, non-canonical nucleotides, and instructions for using the polynucleotide-3' nucleotidyl transferase and non-canonical nucleotides to add a polymer of the non-canonical nucleotides to the 3' end of an RNA. Such a kit may include any of the polynucleotide-3' nucleotidyl transferases and non-canonical nucleotides described in the Methods section above, the descriptions of which are incorporated but not reiterated herein for purposes of brevity.

In certain embodiments, the polynucleotide-3' nucleotidyl transferase is a uridylyltransferase comprising an N-terminal truncation. According to some embodiments, the amino acid sequence of the non-truncated portion of such a uridylyltransferase provided in a kit of the present disclosure is at least 70% identical to the corresponding portion of *Schizosaccharomyces pombe* cid1 (*S. pombe* cid1—SEQ ID NO:1). According to some embodiments, the uridylyltransferase comprises an N-terminal truncation of from 20 to 40 amino acids. In certain embodiments, the polynucleotide-3' nucleotidyl transferase is part of a fusion protein comprising the polynucleotide-3' nucleotidyl transferase and a heterologous sequence of amino acids. When the polynucleotide-3' nucleotidyl transferase is part of such a fusion protein, the heterologous sequence may be any desired length, and in some embodiments is from 5 to 30 amino acids in length. Such a heterologous sequence may be N-terminal to the polynucleotide-3' nucleotidyl transferase portion of the fusion protein. In other embodiments, such a heterologous sequence is C-terminal to the polynucleotide-3' nucleotidyl transferase portion of the fusion protein. According to some embodiments, the heterologous sequence comprises a protease cleavage site within 5 amino acids of the polynucleotide-3' nucleotidyl transferase portion of the fusion protein.

According to some embodiments, the non-canonical nucleotides provided in a kit of the present disclosure comprise one or more types of non-canonical nucleotides selected from inosine, 5-methyluracil (ribothymidine), 4-thiouracil, 6-methyladenine, and 2'-O-methyladenine. In certain embodiments, a kit of the present disclosure includes inosine nucleotides, e.g., for adding a homopolymer of inosines to the 3' end of an RNA or adding a heteropolymer comprising inosines and one or more different non-canonical nucleotides to the 3' end of an RNA.

Components of the kits may be present in separate containers, or multiple components may be present in a single container. For example, in a kit that includes a polynucleotide-3' nucleotidyl transferase and non-canonical nucleotides, the polynucleotide-3' nucleotidyl transferase and non-canonical nucleotides may be provided in the same tube, or may be provided in different tubes. Also by way of example, in a kit that includes two or more types of non-canonical nucleotides, the different types of non-canonical nucleotides may be provided in the same tube, or may be provided in different tubes.

In addition to the above-mentioned components, and as described above, a subject kit may further include instructions for using the components of the kit, e.g., to practice the methods of the present disclosure, e.g., for using the polynucleotide-3' nucleotidyl transferase and non-canonical nucleotides to add a polymer of the non-canonical nucleotides to the 3' end of an RNA. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, Hard Disk Drive (HDD) etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Notwithstanding the appended claims, the present disclosure is also defined by the following embodiments:

1. A method of adding a polymer of non-canonical nucleotides to the 3' end of a ribonucleic acid (RNA), comprising combining:
   an RNA;
   a polynucleotide-3' nucleotidyl transferase; and
   non-canonical nucleotides, in a reaction mixture under conditions in which the polynucleotide-3' nucleotidyl transferase adds a polymer of the non-canonical nucleotides to the 3' end of the RNA.

2. The method according to embodiment 1, wherein the polynucleotide-3' nucleotidyl transferase is selected from the group consisting of: a uridylyltransferase, an adenyltransferase, a guanyltransferase, and a cytosyltransferase.

3. The method according to embodiment 1, wherein the polynucleotide-3' nucleotidyl transferase is a uridylyltransferase.

4. The method according to embodiment 3, wherein the uridylyltransferase comprises an N-terminal truncation.

5. The method according to embodiment 4, wherein the amino acid sequence of the non-truncated portion of the uridylyltransferase is at least 70% identical to the corresponding portion of *Schizosaccharomyces pombe* cid1 (*S. pombe* cid1).

6. The method according to embodiment 4 or embodiment 5, wherein the uridylyltransferase comprises an N-terminal truncation of from 20 to 40 amino acids.

7. The method according to any one of embodiments 1 to 6, wherein the polynucleotide-3' nucleotidyl transferase is part of a fusion protein comprising the polynucleotide-3' nucleotidyl transferase and a heterologous sequence of amino acids.

8. The method according to embodiment 7, wherein the heterologous sequence is from 5 to 30 amino acids in length.

9. The method according to embodiment 7 or embodiment 8, wherein the heterologous sequence is N-terminal to the polynucleotide-3' nucleotidyl transferase portion of the fusion protein.

10. The method according to embodiment 7 or embodiment 8, wherein the heterologous sequence is C-terminal to the polynucleotide-3' nucleotidyl transferase portion of the fusion protein.

11. The method according to any one of embodiments 7 to 10, wherein the heterologous sequence comprises a protease cleavage site within 5 amino acids of the polynucleotide-3' nucleotidyl transferase portion of the fusion protein.

12. The method according to any one of embodiments 1 to 11, wherein a homopolymer of non-canonical nucleotides is added to the 3' end of the RNA.

13. The method according to embodiment 12, wherein the homopolymer is a homopolymer of inosine, 5-methyluracil (ribothymidine), 4-thiouracil, 6-methyladenine, or 2'-O-methyladenine.

14. The method according to any one of embodiments 1 to 11, wherein a heteropolymer of non-canonical nucleotides is added to the 3' end of the RNA.

15. The method according to embodiment 14, wherein the heteropolymer comprises two or more types of non-canonical nucleotides selected from the group consisting of: inosines, 5-methyluracil (ribothymidine), 4-thiouracil, 6-methyladenine, and 2'-O-methyladenine.

16. The method according to embodiment 14, wherein the heteropolymer comprises inosines and one or more non-inosine non-canonical nucleotides.

17 The method according to any one of embodiments 1 to 16, wherein from 5 to 500 non-canonical nucleotides are added to the 3' end of the RNA.

18. The method according to any one of embodiments 1 to 16, wherein from 5 to 100 non-canonical nucleotides are added to the 3' end of the RNA.

19 The method according to any one of embodiments 1 to 18, wherein the RNA combined in the reaction mixture is a polyadenylated RNA.

20. The method according to embodiment 16, wherein the RNA is eukaryotic mRNA.

21. The method according to any one of embodiments 1 to 18, wherein the RNA combined in the reaction mixture is non-polyadenylated RNA.

22. The method according to embodiment 21, wherein the non-polyadenylated RNA is ribosomal RNA.

23. The method according to any one of embodiments 1 to 22, further comprising analyzing the RNA using a nanopore.

24. The method according to embodiment 23, wherein analyzing the RNA comprises identifying the polymer of non-canonical nucleotides added to the 3' end of the RNA.

25. The method according to embodiment 24, further comprising determining the junction between the 3' end of the RNA and the polymer of non-canonical nucleotides to identify the 3' end of the RNA.

26. The method according to any one of embodiments 23 to 25, wherein analyzing the RNA comprises sequencing the RNA or a portion thereof.

27. A kit, comprising:
   a polynucleotide-3' nucleotidyl transferase;
   non-canonical nucleotides; and
   instructions for using the polynucleotide-3' nucleotidyl transferase and non-canonical nucleotides to add a polymer of the non-canonical nucleotides to the 3' end of an RNA.

28. The kit of embodiment 27, wherein the polynucleotide-3' nucleotidyl transferase is selected from the group consisting of: a uridylyltransferase, an adenyltransferase, a guanyltransferase, and a cytosyltransferase.

29. The kit of embodiment 27, wherein the polynucleotide-3' nucleotidyl transferase is a uridylyltransferase.

30. The kit of embodiment 29, wherein the uridylyltransferase comprises an N-terminal truncation.

31. The kit of embodiment 30, wherein the amino acid sequence of the non-truncated portion of the uridylyltransferase is at least 70% identical to the corresponding portion of *Schizosaccharomyces pombe* cid1 (*S. pombe* cid1).

32. The kit of embodiment 30 or embodiment 31, wherein the uridylyltransferase comprises an N-terminal truncation of from 20 to 40 amino acids.

33. The kit of any one of embodiments 27 to 32, wherein the polynucleotide-3' nucleotidyl transferase is part of a fusion protein comprising the polynucleotide-3' nucleotidyl transferase and a heterologous sequence of amino acids.

34. The kit of embodiment 33, wherein the heterologous sequence is from 5 to 30 amino acids in length.

35. The kit of embodiment 33 or embodiment 34, wherein the heterologous sequence is N-terminal to the polynucleotide-3' nucleotidyl transferase portion of the fusion protein.

36. The kit of embodiment 33 or embodiment 34, wherein the heterologous sequence is C-terminal to the polynucleotide-3' nucleotidyl transferase portion of the fusion protein.

37. The kit of any one of embodiments 33 to 36, wherein the heterologous sequence comprises a protease cleavage site within 5 amino acids of the polynucleotide-3' nucleotidyl transferase portion of the fusion protein.

38. The kit of any one of embodiments 27 to 37, wherein the non-canonical nucleotides comprise one or more types of non-canonical nucleotides selected from the group consisting of: inosine, 5-methyluracil (ribothymidine), 4-thiouracil, 6-methyladenine, and 2'-O-methyladenine.

39. The kit of any one of embodiments 27 to 37, wherein the non-canonical nucleotides comprise inosine.

The following examples are offered by way of illustration and not by way of limitation.

EXPERIMENTAL

Example 1—Production and Purification of vCID Uridylyltransferase

Described in this example is the production of a variant *S. pombe* cid1 uridylyltransferase (SEQ ID NO:2—sometimes referred to herein as "vCID") that includes a 37 amino acid N-terminal truncation and N-terminal heterologous sequence that includes a His10 purification tag and TEV protease cleavage site between the tag and the uridylyltransferase.

Plasmid 10H-tev-vCID was made by standard cloning techniques using synthetic DNA. It carries a beta-lactamase gene and a colE1 origin of DNA replication in *E. coli*. *E. coli* BL21(DE3) pLysS cells were transformed with the plasmid and transformants were selected on LB (Luria Broth) agar plates with 100 µg/ml ampicillin at 37° C. overnight. A single colony was used to inoculate 50 mL of LB supplemented with 100 µg/ml ampicillin, shaking at 300 rpm overnight at 37° C. Overnight cultures were diluted to 1L with LB supplemented with 25 µg/ml ampicillin and grown at 37° C. shaking at 300 rpm to $OD_{600}$=0.6. Cells were induced to express vCID by adding IPTG to 1 mM and shaking at 300 rpm for 16-18 hours at 18° C. Cells were harvested by centrifugation at 5000 rpm for 10 minutes, and cell pellets were resuspended in 10 mL of 50 mM Tris-HCl, 1 mM EDTA pH 8.0 and centrifuged again at 4° C. at 5000 rpm for 30 minutes. Supernatant was decanted, and washed pellets were stored at −80° C.

The buffers used for purification contain 50 mM $NaH_2PO_4$, 300 mM NaCl, 100 mM KCl, 1 mM DTT, 10% glycerol and various concentrations (10-500 mM) imidazole. Frozen pellets were resuspended in 14 mL of 10 mM imidazole buffer with 1 mg/ml lysozyme, 0.5 mM PMSF, and 3 units/mL benzonase nuclease, then incubated on ice for 5 minutes. Cells were lysed with glass bead vortexing for 3 minutes in 15 second intervals. Cells were incubated on ice for 15 seconds between vortexing. Lysates were clarified by centrifugation at 14000×g for 1 hour at 4° C. Resulting supernatant was incubated for 30 minutes with 2.5 mL of cobalt-chelate resin (pre-equilibrated in 10 mM imidazole buffer) with gentle shaking at 4° C., and then poured into a column. The column is washed 2× with 12 mL of 20 mM imidazole buffer, and 1× with 5 mL of 50 mM imidazole buffer. Eluates were collected using 100 mM, 150 mM, 200 mM, 250 mM, 400 mM, and 500 mM imidazole buffers at 5 mL each in succession.

Each eluted sample was concentrated in a protein concentrator tube (Millipore) until the total volume is <500 µL. The samples were resuspended in 10 mL storage buffer (10 mM Tris-HCl PH 7.5, 100 mM NaCl, 1 mM DTT, 0.1 mM EDTA, 50% glycerol v/v), and concentrated again until the sample volume was <500 µL. FIG. 1 is an example of the purified vCID protein separated on an SDS-PAGE.

To determine apparent size of the vCID protein, the migration distance was plotted vs the log of the molecular weight of the standards on semilogarithmic graph paper to create a standard curve. The migration distance of vCID was determined and the position at which this distance intersects the standard curve gives an apparent molecular weight of 44 kDa, in good agreement with the predicted molecular weight of 44.9 kDa (FIG. 1).

Example 2—Inosine Tailing Using vCID

Figure 2:
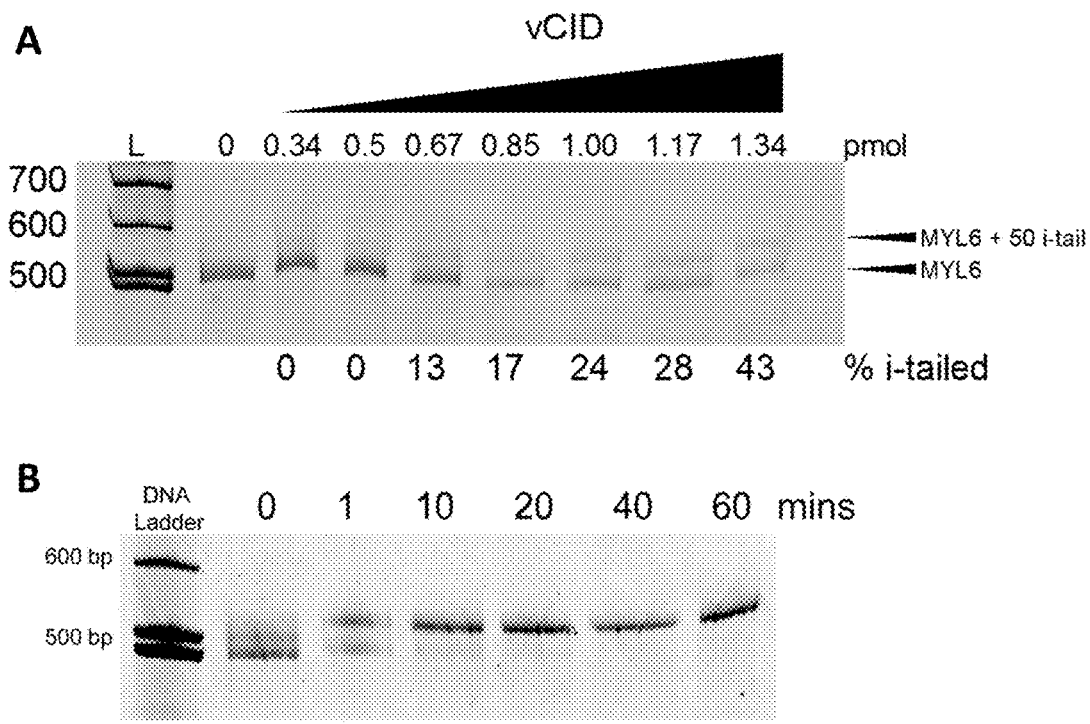
FIG. 2: Panels A and B provide data demonstrating the addition of inosine homopolymers to the 3' ends of RNAs according to some embodiments of the present disclosure.
Figure 3:
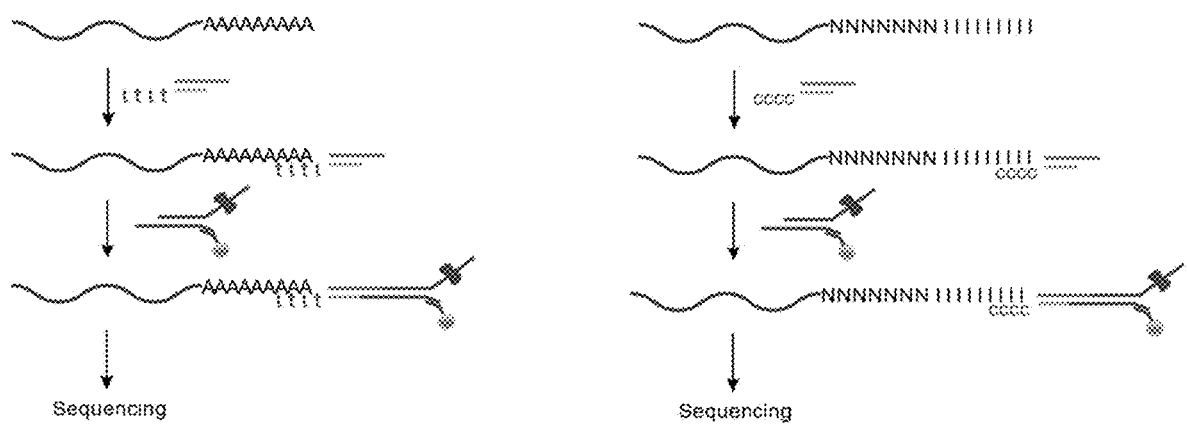
FIG. 3: Schematic illustration of previous approaches for nanopore-based analysis of polyadenylated RNAs (left) and a nanopore-based analysis of polyadenylated RNAs according to one embodiment of the present disclosure (right). According to this example embodiment, a homopolymer of inosines is added to the 3' end of a polyadenylated RNA. A nanopore sequencing adapter is then attached to the inosine homopolymer via hybridization of a stretch of complementary nucleotides (cytosines in this example) to a stretch of the inosine homopolymer. Upon attachment of the sequencing adapter, the RNA (with inosine homopolymer) is ready for downstream analysis using a nanopore-based analysis device, e.g., nanopore sequencing device.

This example demonstrates the addition of an inosine homopolymer to the 3' ends of poly(A)-tailed RNA molecules (sometimes referred to herein as "tailing"). To add a ~50 inosine homopolymer on the 3' end of a poly(A)-tailed RNA molecule, RNA in 0.1 mM EDTA to a final volume of 2.95 µL is denatured at 95° C. for 2 minutes then placed on ice for 2 minutes. The RNA is added to a reaction containing 4 mM ITP, 50 mM NaCl, 13.5 mM $MgCl_2$, 1 mM DTT, BSA 500 µg/ml, pH 7.9, and >1 pmol vCID in a final volume of 7.5 µl and incubated at 37° C. for 1 hour. The RNA was isolated from the reaction, run on a denaturing urea-polyacrylamide gel, stained with Sybr-Gold and scanned on a Typhoon scanner. FIG. 2, panel A, shows an example inosine tailing ("i-tailing") reaction. Data from a second i-tailing at various time points is shown in FIG. 2, panel B.

For data capture and analysis, inosine tailing efficiency was determined by Quantity One volume analysis. Rectangular boxes of equal size were drawn around each product band. Local background was subtracted, and the adjusted volume (signal) from each product was normalized by size (larger products are brighter because they bind proportionately more dye) and molar ratios were calculated. These values were used to calculate percentage of molecules that received a tail. Under certain conditions, all the input MYL6 molecules received a ~50 nt inosine tail.

Example 3—Nanopore Analysis of Inosine-Tailed RNA

Figure 4:
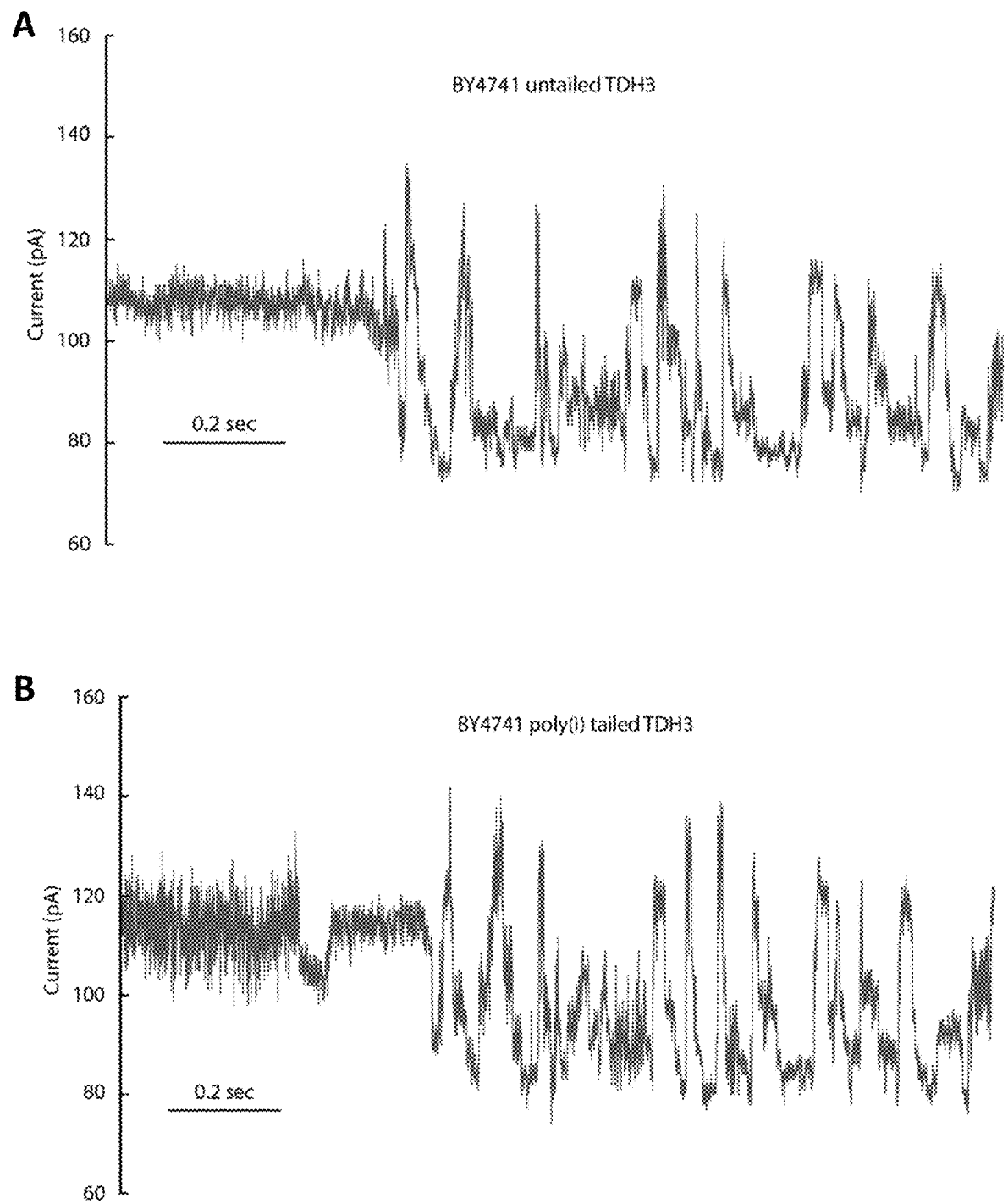
FIG. 4: Raw nanopore current traces of the TDH3 gene from yeast BY4741. The upper trace is untreated poly(A) RNA and the lower trace is poly(I)-treated poly(A) RNA. The traces show a current change for the poly(I) extension that is readily distinguishable from a natural poly(A) tail.

A nanopore sequencing adapter was attached to the inosine homopolymer of inosine-tailed RNAs produced according to Example 2 via hybridization of a stretch of complementary nucleotides (cytosines in this example) to a stretch of the inosine homopolymer. Upon attachment of the sequencing adapter, the RNA (with inosine homopolymer) was subjected to nanopore-based analysis using an Oxford Nanopore Technologies nanopore sequencing device. Shown in FIG. 4 are raw nanopore current traces of the TDH3 gene from yeast BY4741. The upper trace is untreated poly(A) RNA and the lower trace is poly(I)-treated poly(A) RNA. The traces show a current change for the poly(I) extension that is readily distinguishable from a natural poly(A) tail.

Figure 5:
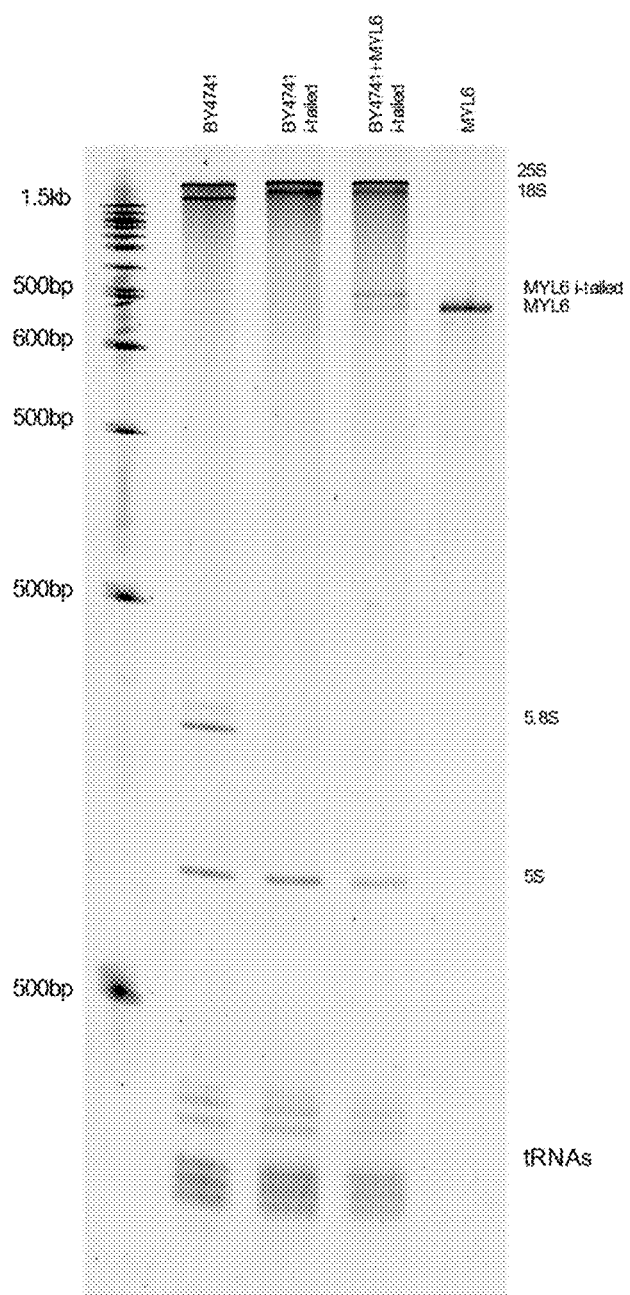
FIG. 5: Data for yeast BY4741 total RNA with inosine tailing treatment. Poly(A) MYL6 T7 transcript was used as a control. The data demonstrate a strong stop of inosine tails on poly(A) RNAs.
Figure 6:
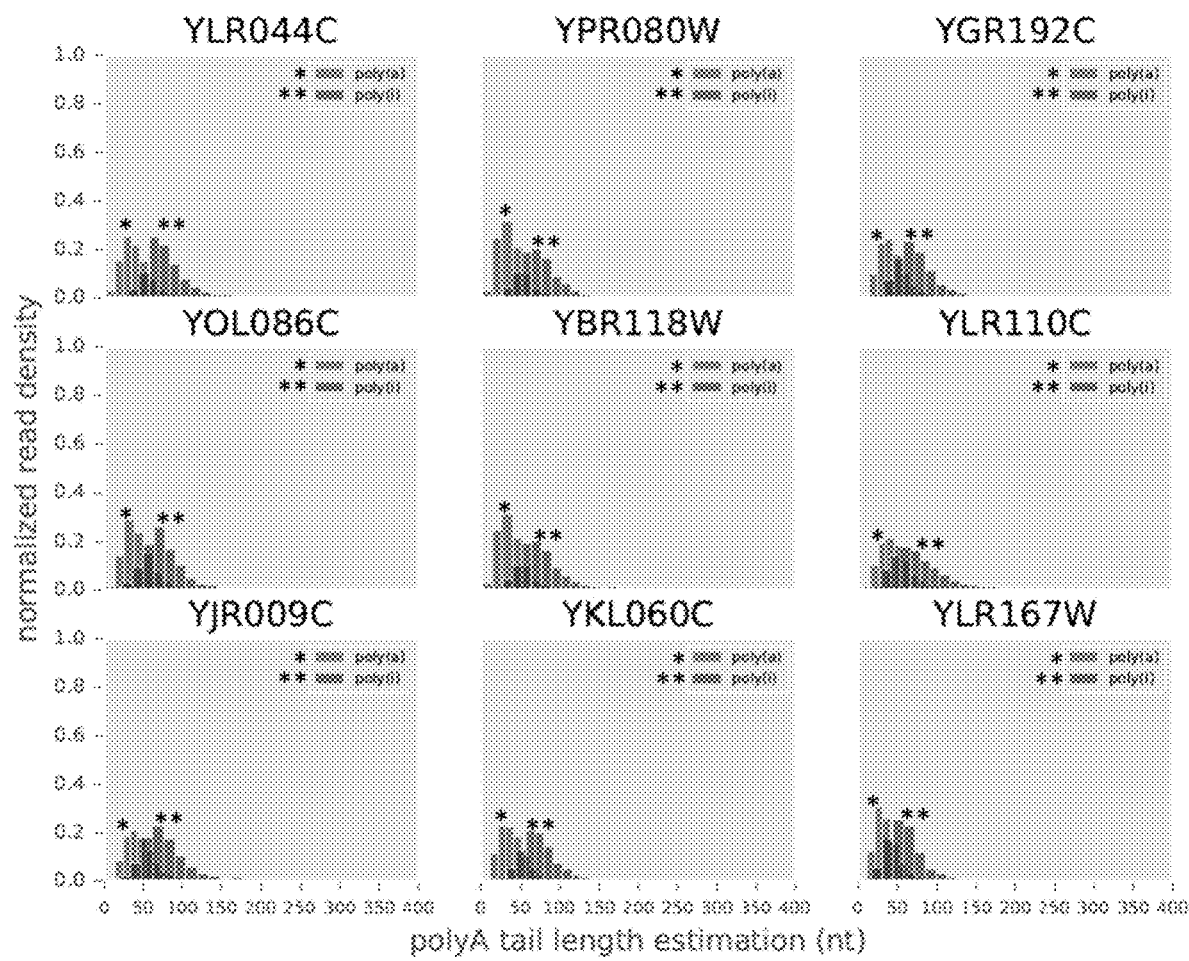
FIG. 6: Data for the nine most covered yeast BY4741 genes. Nanopolish polyA estimates an ~40 nt increase in homopolymer tail length for poly(I) tailed samples.
Figure 7:
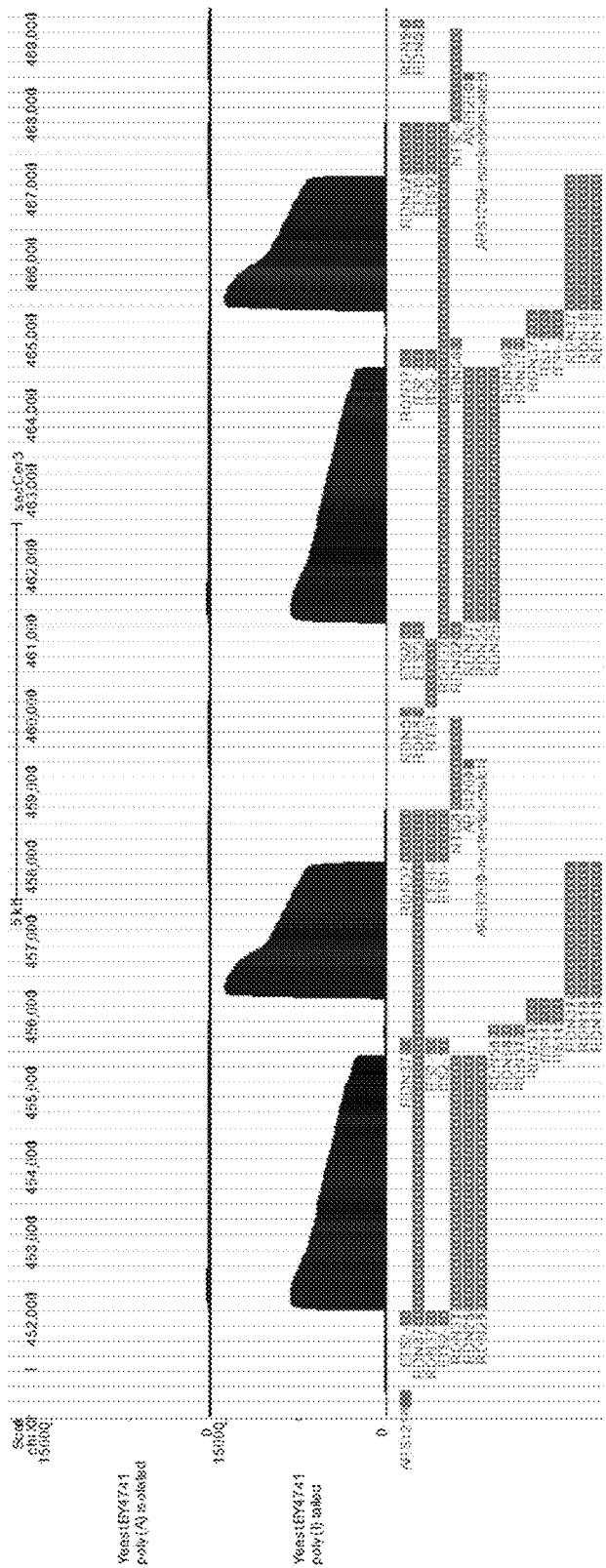
FIG. 7: Data demonstrating the proportion of RNA type reads from poly(A) isolated and poly(I) treated yeast BY4741 Total RNA. rRNA make up the highest number of reads in poly(I) treated RNA.
Figure 7:
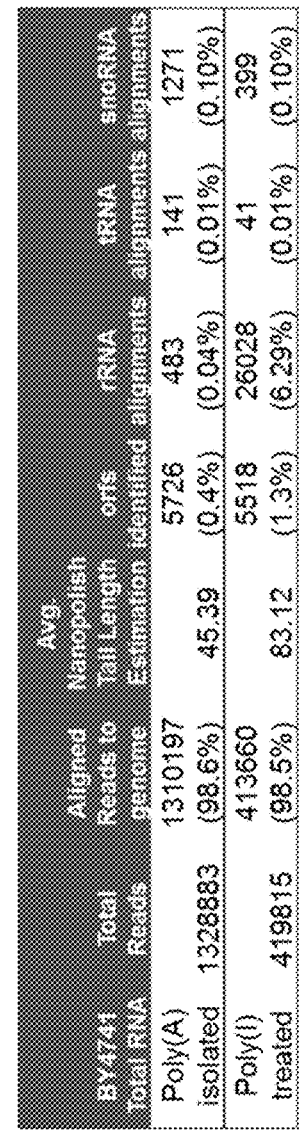

FIG. 5 provides data for yeast BY4741 total RNA with inosine tailing treatment. Poly(A) MYL6 T7 transcript was used as a control. The data demonstrate a strong stop of inosine tails on poly(A) RNAs. Shown in FIG. 6 is data for the nine most covered yeast BY4741 genes. Nanopolish polyA estimates an ~40 nt increase in homopolymer tail length for poly(I) tailed samples. FIG. 7 shows data demonstrating the proportion of RNA type reads from poly(A) isolated and poly(I)-treated yeast BY4741 total RNA. rRNA makes up the highest number of reads in poly(I) treated RNA.

Figure 8:
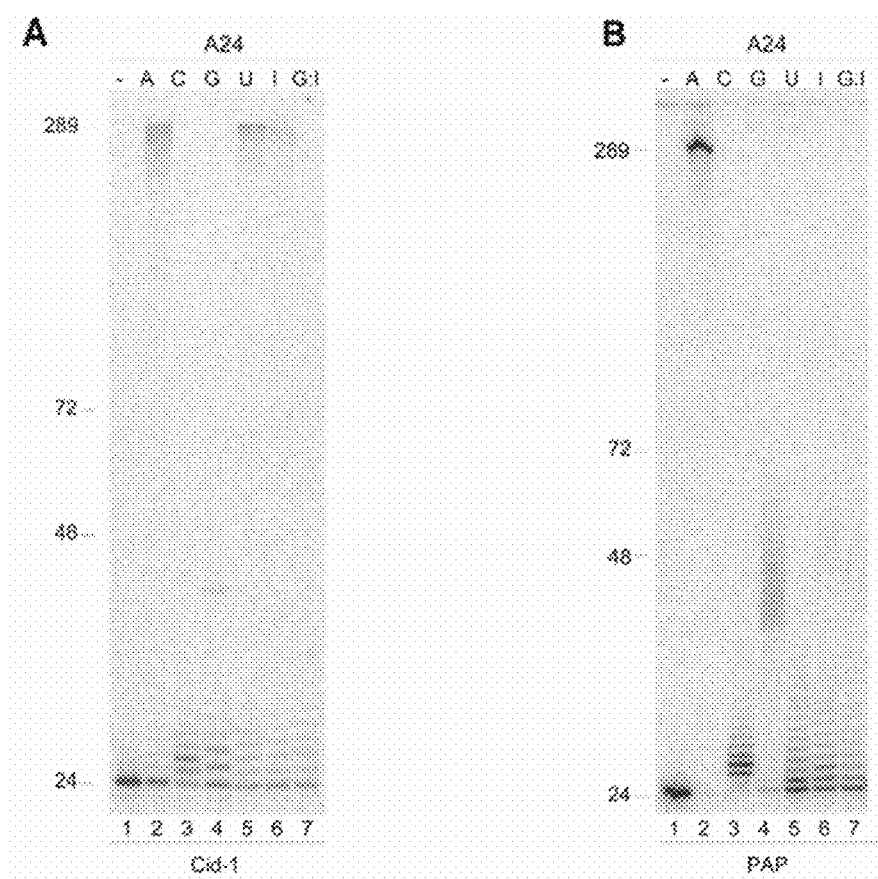
FIG. 8: A test of commercial preparations of two enzymes for their ability to add nucleotide homopolymers to the 3' end of different RNAs. Incorporation of rNMPs onto the 3' end of $^{32}$P-5' end-labeled A24 RNA using (Panel A) Cid-1 PolyU polymerase from New England Biolabs and (Panel B) PolyA polymerase from ThermoFisher. Incorporation of AMP, UMP, and IMP onto the 3' ends of MYL6(A+) and MYL6(A−) using (Panel C) Cid-1 PolyU Polymerase from New England Biolabs and (Panel D) PolyA Polymerase from ThermoFisher. (Panel E) Incorporation of modified-UTPs and mixtures of modified-UTPs and UTP onto the 3' ends of MYL6(A+) using Cid-1.
Figure 8:
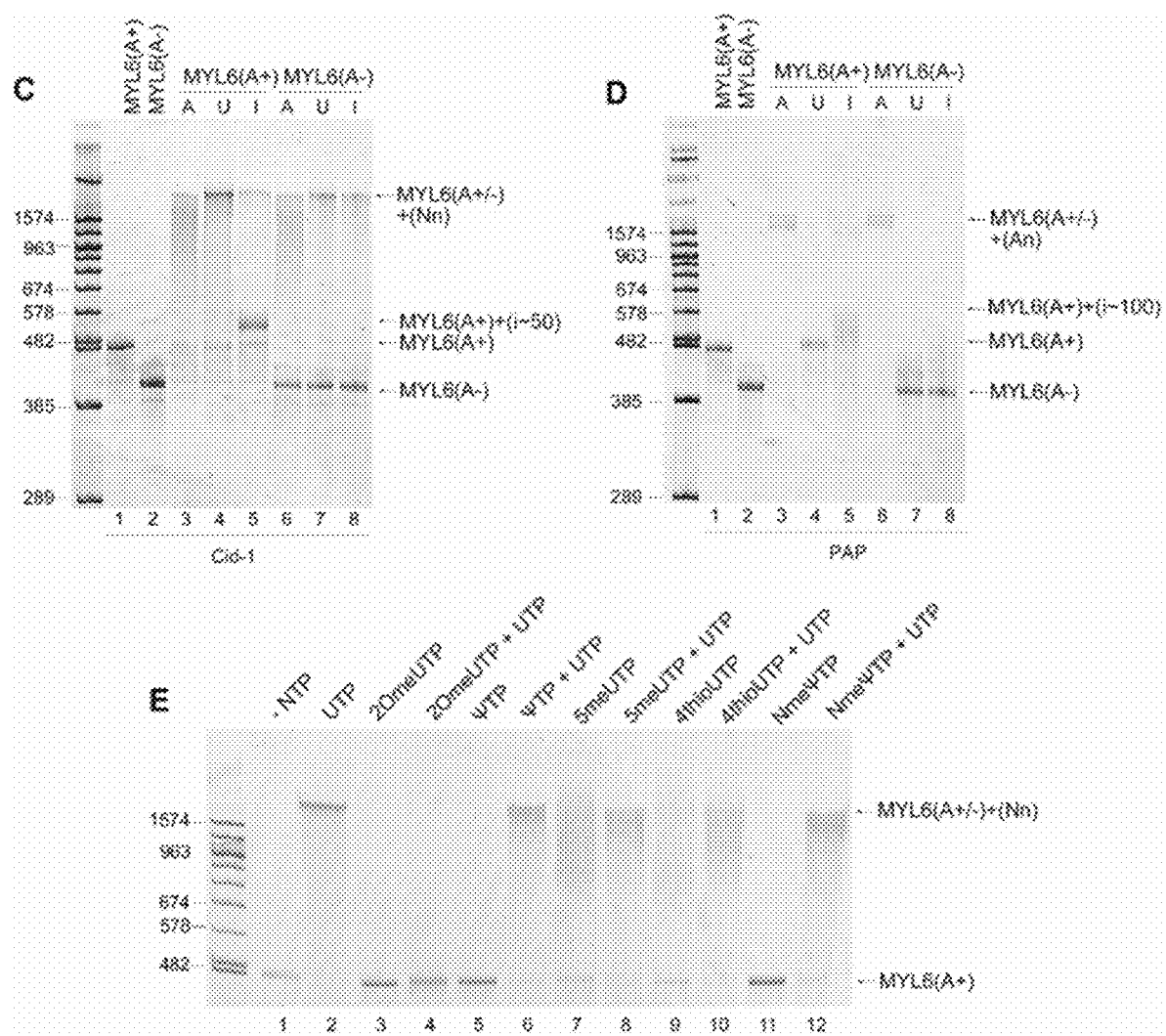

Example 4—Cid-1 polyU Polymerase can Efficiently Add Inosines to the 3' Ends of Different RNA Molecules To develop methods for adding modified nucleotides to the 3' ends of RNA, commercial preparations of two well-studied enzymes, the *S. pombe* polyU polymerase Cid-1, and *S. cerevisiae* polyA polymerase (PAP), were tested. It was first determined that these commercial preparations had the expected nucleotide adding specificities by incubating them with various rNTPs and a 24-nucleotide oligomer of adenosine (A24) under the reported conditions. This test (FIG. 8, panels A and B) shows that each commercial preparation behaves as originally described. Briefly, Cid-1 from New England Biolabs efficiently adds U and A, but only poorly adds C or G (FIG. 8, panel A), in agreement with previous work. PAP from ThermoScientific efficiently adds A, and to a much lesser extent G, but only poorly adds U or C, as observed previously. Also examined was the ability of each enzyme to use inosine triphosphate (ITP, a purine similar to G) to make poly-inosine tails (FIG. 8). It was found that Cid-1 can add long stretches of inosine to A24 (FIG. 8, panel A, lane 6) whereas PAP was only able to add a few residues (FIG. 8, panel B, lane 6). It was concluded that the commercial preparations faithfully reproduce the published activity of each enzyme using the four standard rNTPs. Furthermore Cid-1 efficiently adds the modified base inosine to the A24 substrate, whereas PAP only does so inefficiently.

To test these enzymes with substrates more representative of those found in natural samples, prepared were model mRNAs based on MYL6 mRNA with (MYL6(A+)) or without (MYL6(A−)) a pre-existing 40 nucleotide polyA tail, to represent polyadenylated mRNAs and non-polyadenylated RNAs. Cid-1 used U and A to make long tails on both model RNAs (FIG. 8, panel C). Unexpectedly, Cid-1 uniformly added about 50 inosine residues to a majority of MYL6(A+) molecules, but also produces some molecules with long (>200 nt) tails (FIG. 8, panel C, lane 6). In contrast, Cid-1 only inefficiently adds long tails (it appears to act processively on just a few molecules of MYL6(A−)) (FIG. 8, panel C, lane 9).

In comparison, PAP efficiently added polyA to both MYL6(A+) and MYL6(A−) RNAS, but only poorly added U to either (FIG. 8, panel D, compare lanes 3 and 4 to lanes 6 and 7). The presence of a polyA tail on MYL6(A+) appears to allow PAP to add short heterogenous stretches of I (FIG. 8, panel D, lane 5) but without a polyA tail MYL6(A−) is much less efficiently used (FIG. 8, panel D, lane 8). When Cid-1 and PAP were tested using a shorter model mRNA with 44A residues (Gluc200(A+)) or without an polyA tail (GLuc200(A−)), similar results were observed with A and U, but Cid-1 did not add a +50 inosine tail to this RNA (data not shown), similar to the result with A24 (FIG. 8, panel A, lane 6), suggesting that an RNA of a certain size may be necessary for producing the +50 product. It was concluded that the presence of a pre-existing polyA tail significantly promotes the use of an RNA as a substrate for both enzymes, except that RNAs below a certain size or with other as yet unidentified features may be poor substrates.

Given that Cid-1 adds a +50 I-tail on a model mRNA but inefficiently adds I-tails on complex RNAs (FIG. 8, panel C, lane 5 and 8), the ability of Cid-1 to add modified U residues to a model mRNA was tested (FIG. 8, panel E). It was considered that its native uridylation activity might favor the incorporation of modified Us on a wider variety of RNAs. Reactions were set up with modified-UTPs alone, and with a mixtures of modified-UTP and UTP. Cid-1 was unable to use 2'-O-methyl-UTP whether or not UTP is added in the reaction (FIG. 8, panel E, lane 3 and 4), suggesting that it is a competitive inhibitor of UTP addition, likely occupying the binding site but blocking catalysis. Surprisingly, Cid-1 also did not use YTP, but worked well with a mixture (FIG. 8, panel E, lanes 5 and 6). Similar results were found with NmeΨTP and NmeΨTP:UTP (FIG. 8, panel E, lanes 11 and 12), suggesting that these modified UTPs do not bind well to the UTP binding site and thus do not act as competitive inhibitors. Both 5meUTP and 4thioUTP can be used by Cid-1, producing long tails with or without the addition of UTP (FIG. 8, panel E, lanes 7, 8, 9, 10). It was surprising that YTP and NmeΨTP appear not to be used by Cid-1 given that it uses 5meUTP. All three modified bases differ at the same position in the base (in pseudouridine the N1 position occupies the same location as the C5 of uridine). The enzyme therefore seems sensitive to the flipped orientation of pseudouridine analogs. It was concluded that ability of Cid-1 to use certain modified UTPs to add polymers of uncommon nucleotides to the ends of natural RNAs illustrates additional potential for development of the methodology for nanopore RNA sequencing, including mixing and co-sequencing two libraries with different homopolymers as a kind of barcoding strategy. It was concluded that in addition to inosine, modified uridine and perhaps many other modified bases may provide a wealth of experimental flexibility in the application of modified nucleotide homopolymer tags for a variety of RNA studies.

Example 5—Optimization of the Cid-1 Inosine Tailing Reaction for Nanopore Library Preparation Based on the results in the preceding example, optimization and validation of the inosine tailing reaction catalyzed by Cid-1 was performed. To evaluate the capacity of the Cid-1 reaction to modify amounts of RNA necessary for Direct-RNA Nanopore library construction, MYL6(A+) was incubated with Cid-1 and ITP under different conditions, and production of the ~50 I-tailed product (FIG. 9, panels A and B) was measured. It was determined that Cid-1 reacts immediately after being introduced to the reaction mixture ("0" time) and the reaction is complete by 40 minutes. Cid-1 likely acts processivity, since the ~+50 product accumulates rapidly without prior accumulation of intermediate length products between +0 and ~+50. Most RNA molecules are found in one of two distinct classes: unreacted (+0) and completely reacted (~+50) extended form throughout the reaction time (FIG. 9, panel A), suggesting substrate is bound, ~50 inosines are added by the enzyme without dissociation, until the reaction is complete. Under optimal conditions, 1.2 pmol of RNA ends can be reacted with 2 units of Cid-1 from NEB (FIG. 9, panel B) to convert nearly all input molecules to the ~+50 form (FIG. 9, panel B).

Figure 9:
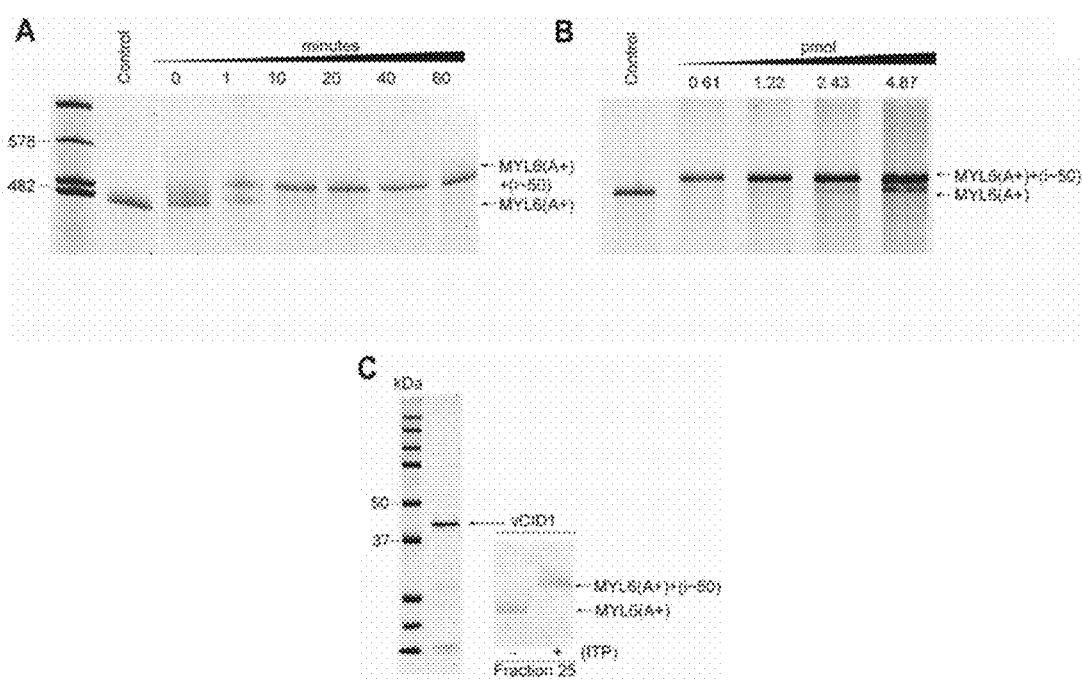
FIG. 9: Cid-1 can uniformly tail microgram amounts of polyA RNA with ~50 inosine residues. Using MYL6(A+) (Panel A) Time-course of 0-60 minutes for the rate of the reaction (Panel B) and input titration. (Panel C) SDS-PAGE of purified vCID1 and I-tailing activity on MYL6(A+) (Panels D-F) RNase A digestion of inosine-tailed and untailed $^{32}$P-pCp-labeled MYL6(A+), MYL6(A−) and 5.8S.
Figure 9:
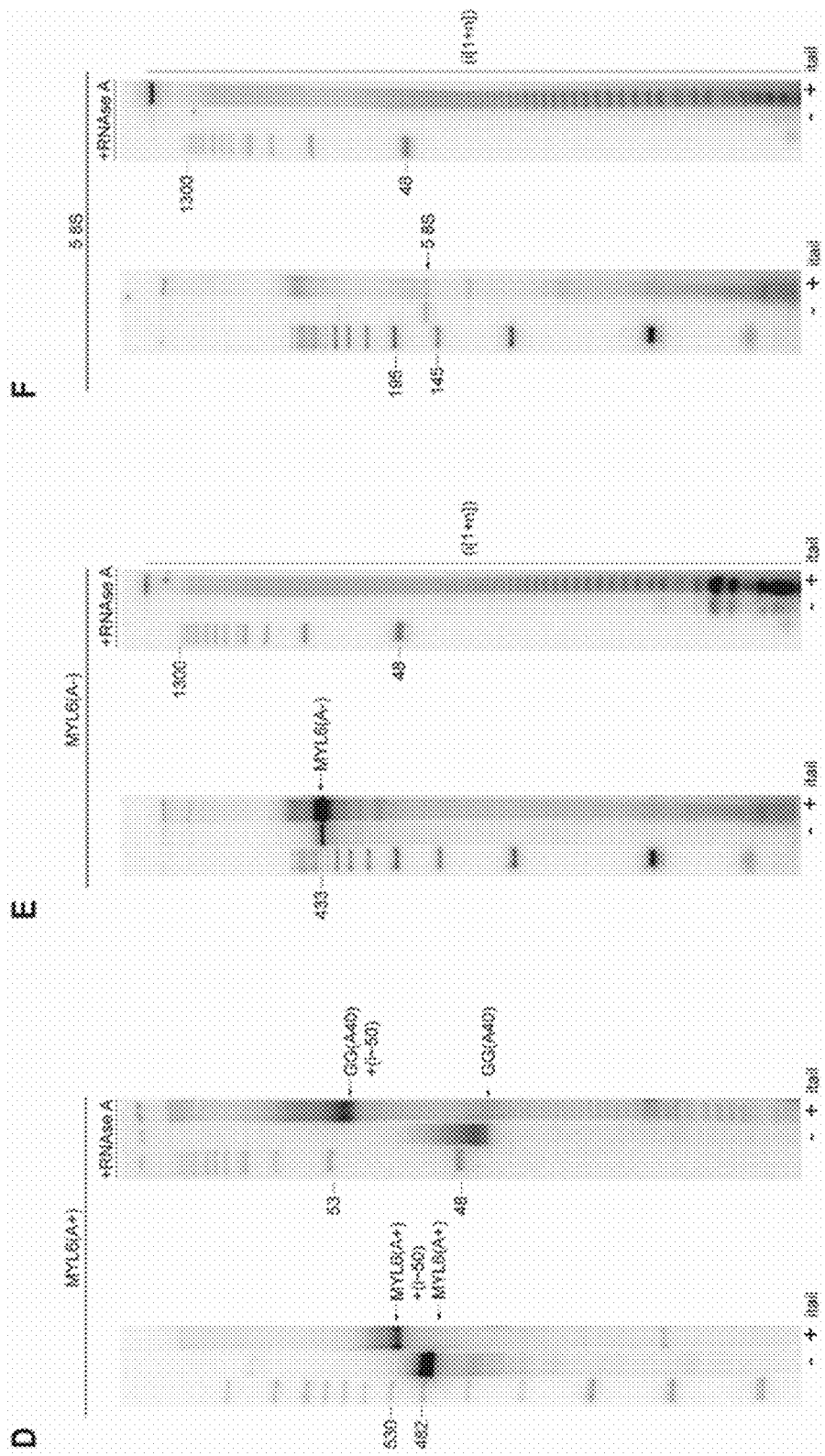

To confirm for future studies that this property is a feature of native Cid-1 and not generated by an unknown step in the commercial preparation of the enzyme, a recombinant Cid-1 truncated 26 nucleotides from the C-terminus (vCID1) was cloned, expressed and FPLC purified in *E. coli*, where it was found that the addition of ~50 inosines to MYL6(A+) is a natural property of the enzyme (FIG. 9, panel C). It was concluded that Cid-1 provides an avenue to create Direct-RNA Nanopore sequencing libraries in which the natural end of an RNA may be distinguished by the junction between the natural sequences and the non-standard nucleotide (in this case inosine) homopolymer.

To precisely measure the length of the ~+50 extension of RNA catalyzed by Cid-1, various inosine-tailed (and untailed control) molecules were labeled at their 3' ends with $^{32}$P-pCp using RNA ligase, and then digested with RNAseA, which cuts only after pyrimidines, leaving homopurine polymers like the polyA tail, or a polyI tail intact (FIG. 9, panels D, E and F). For example, MYL6(A+) contains two Gs at its 3' end to which the 40 nucleotide polyA tail is added, creating an RNAseA resistant product that is exactly 42 nucleotides in length (FIG. 9, panel D). Measured was the RNAseA digested I-tailed MYL6(A+) product and estimate that the unreacted MYL6(A+) tail is 43 nucleotides (including the ligated $^{32}$P-pCp-labeled residue) long, whereas the I-tailed MYL6(A+) is calculated to be 93.4 nucleotides. Thus, the calculated difference of 50.4 nucleotides indicates that most mRNA molecules carry 50 inosine residues after the Cid-1 reaction.

The non-polyadenylated RNAs MYL6(A-) and yeast 5.8S rRNA do not acquire a uniform 50 nt polyI extension; rather, a heterogeneous long I-tail is added (FIG. 9, panel C and data not shown). Accordingly, RNaseA digestion of $^{32}$P-pCp labeled Cid-1 product generates a ladder of RNAse-resistant products that extends far up the gel. It was concluded that polyA+ RNAs generally acquire a uniform 50 nt inosine extension whereas the non-polyadenylated RNAs in a sample acquire inosine tails of a wide variety of lengths from a few to >1000 nt (FIG. 9, panels D and F).

Figure 10:
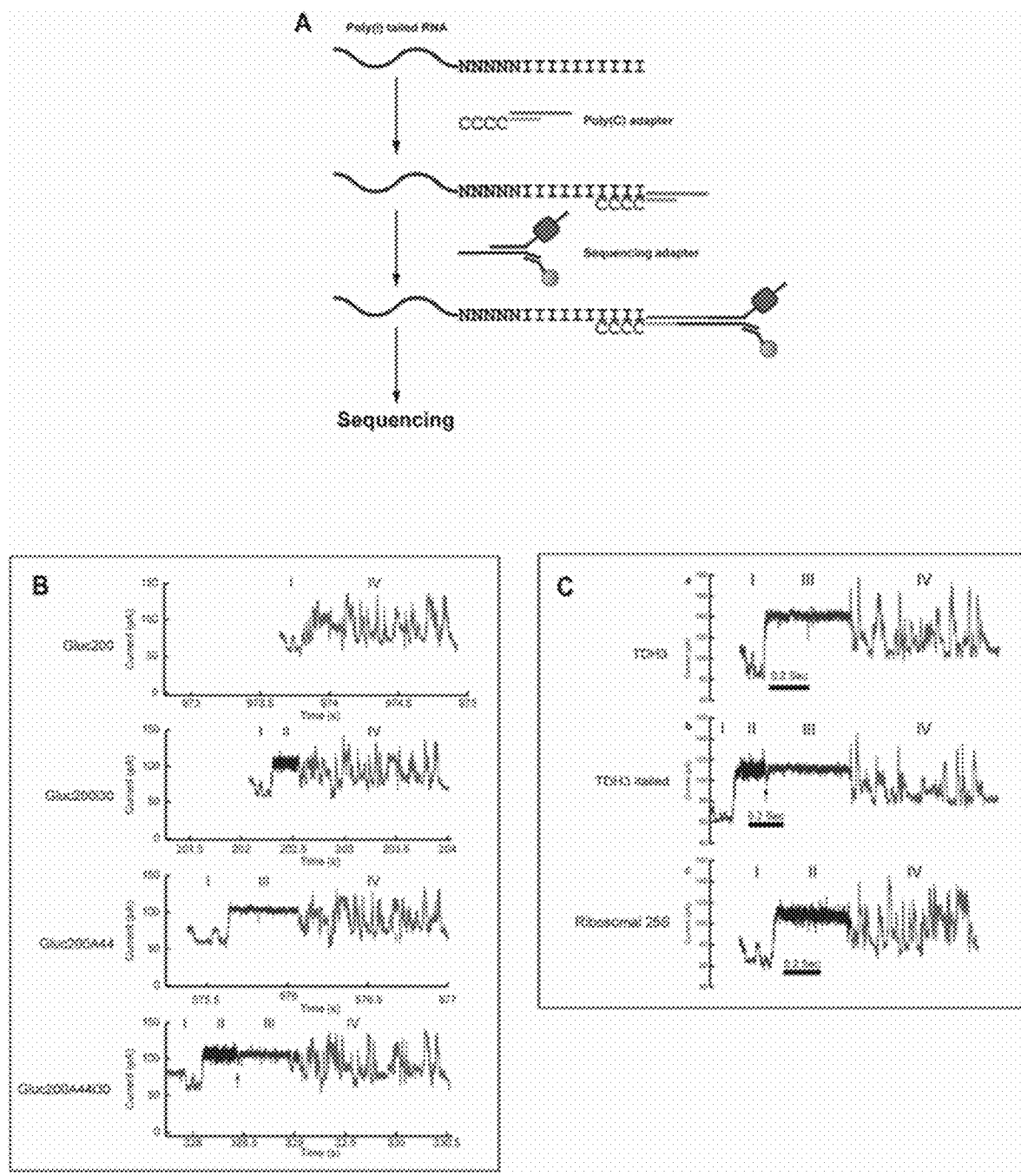
FIG. 10: Inosine tails generate a distinct signal in the nanopore during sequencing. (Panel A) Library preparation method for poly(I) sequencing. (Panels B-C): Example current traces with signals I. Sequencing Adapter II. PolyI III. PolyA IV. 3' native sequence of the RNA (Panel B) Raw current traces of control samples Gluc200 and GLuc200A44 containing unligated and ligated 30 nt inosine homopolymer tail (Panel C) Example traces of mRNA TDH3 found in polyA and polyI sequencing, and non-adenylated 25S RNA in polyI sequencing.

Example 6—Inosine Tails Generate a Distinct Signal in the Nanopore During Sequencing Adapting an RNA molecule for direct RNA sequencing by nanopore requires hybridization of the target RNA to a DNA splint, followed by ligation of the RNA 3' end to one strand of the DNA adaptor. To capture inosine-tailed RNA molecules for analysis in the nanopore, a custom adaptor with a polyC segment of 10 residues that would base pair with the inosine tail was used, to promote ligation of the RNA 3' end to the nanopore sequencing adaptor (FIG. 10, panel A). This allowed signals from inosine-tailed molecules by direct nanopore sequencing to be obtained (FIG. 10, panels B and C).

It was hypothesized that tailing with non-standard (other than A, G, C, or U) RNA nucleotides might produce electronic signals in the pore that would differ from those produced by polymers of the standard nucleotides, in particular the polyA tails found on many natural RNAs. To determine whether this is the case, ONT's standard Direct-RNA Nanopore sequencing method was modified using the custom cytosine splint adapter ligation (FIG. 10, panel A) and sequencing libraries from synthetic and natural RNA samples were created. To identify distinct polyI signals appended to signals from a known RNA sequence, prepared were control samples of GLuc200(A+) and GLuc200(A-) with or without a splint-ligated 30 nt polyI homopolymer, libraries using the appropriate adaptor oligonucleotide were created, and the libraries were sequenced in the Nanopore using poly(C) adapters. The raw current trace of a single representative molecule from each library is shown in (FIG. 10, panel B). Direct RNA sequencing in the ONT nanopore format used here threads the 3' end of the RNA into the pore first, and the current (in picoamperes) across the pore is shown in the y-axis with time displayed on the x-axis, thus tracing the current as the molecule transits the pore from the 3' to the 5' end over time. The part of the trace corresponding to the adaptor is segment I, the part corresponding to the GLuc200 sequence is segment IV, the part corresponding to polyA is segment III, and the part corresponding to polyI is segment II. The top panel shows GLuc200(A-) with no I-tail, showing that after the adaptor sequence, a trace consistent with an RNA of complex sequence follows immediately. GLuc200(A+) on the other hand shows a monotonic signal at slightly above 100 pA in this experiment before the appearance of the complex sequence trace. The inosine-tailed molecule Gluc200(A-)i30 also shows a monotonic signal between the adaptor and the complex sequence trace at just above 100 pA, yet this appears distinct from that observed on Gluc200(A+). This distinction is even more clear in the Gluc200(A+)i30 molecule to which the inosine tail is added 3' to the polyA tail: following the adaptor the monotonic inosine signal is followed by the monotonic polyA signal, and then finally the complex sequence trace of Gluc200. Although the polyI and polyA signals have a similar mean current of just above 100 pA, the variation in mean current is substantially different, with polyI currents wavering across an approximately 20 pA window, and polyA providing more narrow variation. In addition, there is a peculiar drop (marked as an arrow) in the current amplitude during the transition from the polyI to the polyA homopolymeric segments.

To explore how the distinct poly(I) signal may be useful in characterizing biological samples, poly(A) RNA enriched samples of yeast BY4741 RNA and Human Cell line RNA GM12878 were tailed (not shown), and libraries using the polyC adaptor were prepared. For comparison, standard libraries for poly(A) RNAs were made using the adaptor provided by ONT. Shown as an example is the TDH3 gene and 25S rRNA from *Saccharomyces cerevisiae*. When comparing the raw current traces of the polyI tailed and the polyA reads, a distinctive raw current segment is observed at the transition of the 3' end of the polyA homopolymer signal and the adapter that is not seen in any of the raw current traces of the standard polyA libraries. (FIG. 10, panel C). The placement of the new signal indicates that this is a modification of the RNA from the incorporation of the inosine homopolymer. The poly(I) signal is observed to have the same mean current amplitude but different RMS noise of the polyA signal, and there is a peculiar drop in the current amplitude in the transition of the poly(I) to the poly(A) signal found in all the reads of the poly(I) libraries. It was concluded that an inosine homopolymer has a distinct trace on the raw current signal that can be distinguished from the polyA tail, therefore preserving the true length of the pre-existing polyA tail and also differentiate polyA RNA from non-polyA RNA in sequencing data.

Figure 11:
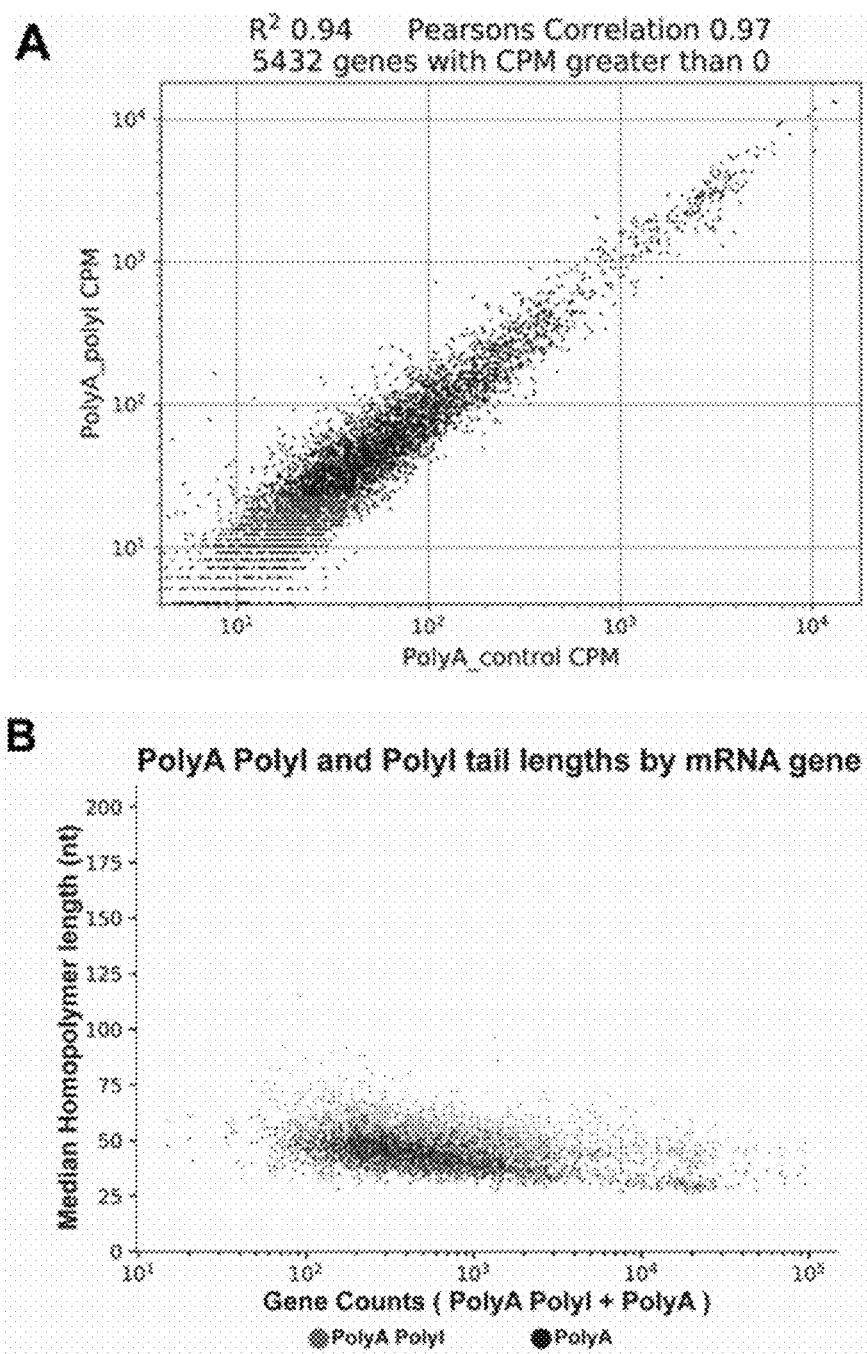
FIG. 11: Detection and abundance estimates for polyA mRNAs using I-tailing are equivalent to the standard library method. (Panel A) R2 value plots of poly(I) and poly(A) (Panel B) plots of median nanopolish estimated tail length of mRNA encoding genes in poly(I) and poly(A) sequencing. method (Panel C) histograms of nanopolish homopolymer length of the top 4 covered genes in poly(I) and poly(A) sequencing.
Figure 11:
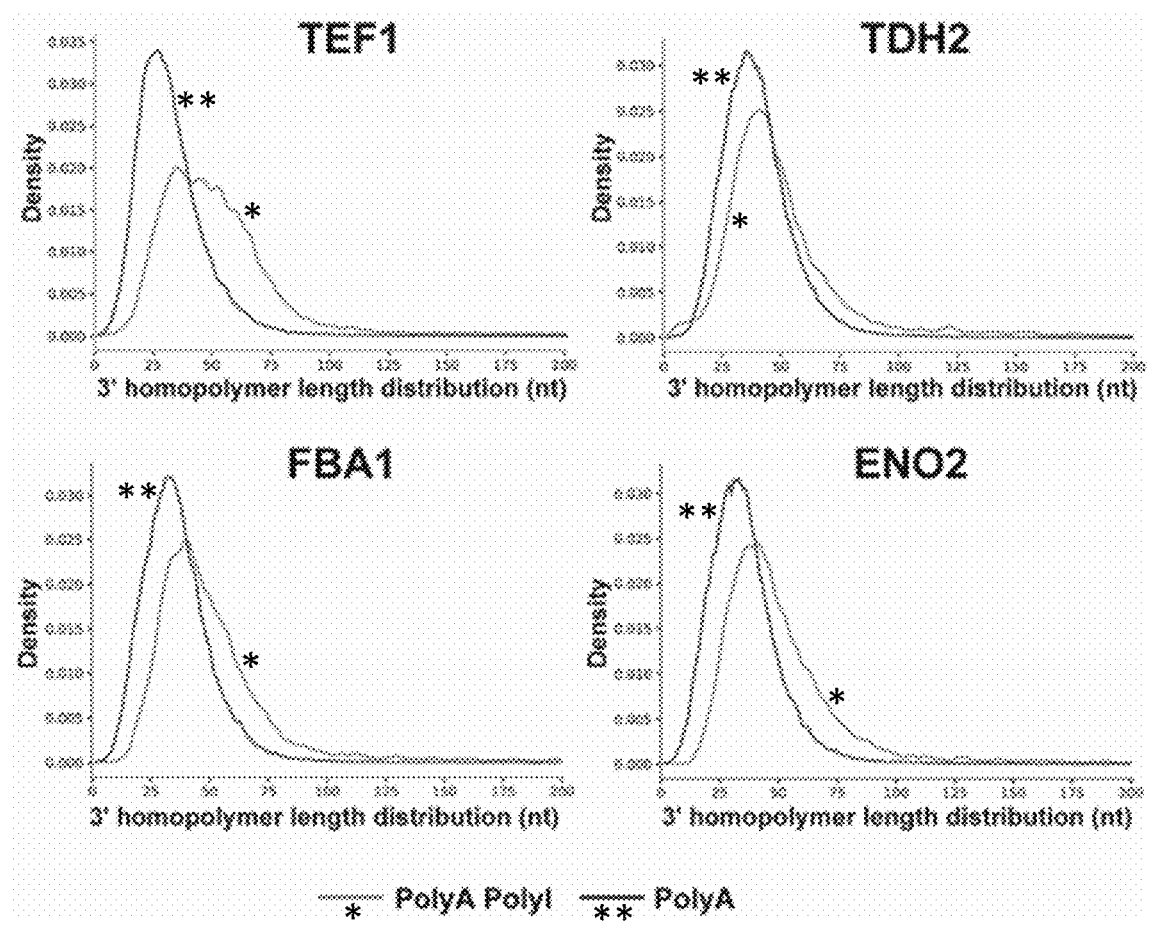

Example 7—Detection and Abundance Estimates for polyA mRNAs Using I-Tailing are Equivalent to the Standard Library Method To ensure that the polyI method is not introducing bias in sequencing, a regression analysis was performed comparing the gene coverage of polyA and polyI-tailed polyA libraries of yeast BY4741 RNA, by plotting the counts per million (CPM) of found genes in the polyA control reads in the x-axis, against the CPM of found genes in the polyI-tailed libraries in the y-axis. The plot indicates a R2 of 0.94 and Pearson's Correlation of 0.97 (FIG. 11, panel A). The high correlation between both samples indicate similar gene coverage. Even though PolyI sequencing generates ~10-20% of the number of reads compared to polyA sequencing (data not shown), it was seen that even with the low number of reads the proportion of the gene populations in the sample is not significantly affected.

To determine how the analysis of the nanopore signals compares with the obtained knowledge that Cid-1 is adding short (+50) I-tails onto mRNAs, the polyI extension and the natural polyA tail length of the mRNAs were estimated using Nanopolish, a commonly used software package that can estimate polyA tail lengths using ONT nanopore sequencing data. Nanopolish is unable distinguish the polyI from the polyA signal in each read, and thus only provides an estimate of the length of the sum of both homopolymers. To determine how the software estimates the length of the polyI tails, compared were the median tail lengths estimated by Nanopolish of the same mRNAs from the standard polyA-sequenced to the polyI-tailed polyA libraries. On a plot, the genes were ordered by the sum of the reads found for each gene, going from least number of reads to highest number reads on the x-axis. On the y-axis, plotted were the Nanopolish-called median tail length estimate for the genes of the polyI tailed reads and the genes of the control polyA reads (FIG. 11, panel B), where the genes of the polyI tailed reads were generally clustered above the genes of the control polyA reads. It was determined that this arrangement is appropriate, as the regression analysis showed that the number of reads is about the same in both samples. The majority of the polyA control median homopolymer estimates are in the 40-60 nucleotide range, as found previously for yeast mRNAs. For the polyA+ polyI library reads, Nanopolish calls a ~+25 nucleotide increase for all the reads, with majority of the plots ranging from 50-75 nucleotides. For lower expressed genes, there is a higher variability in median added length due to polyI, and there are a few genes with tails that extend up to ~100-125 nucleotides in total length. In more highly expressed genes, observed was a shift to a tighter distribution where most of the reads are in the lower ranges stated above. In conclusion, genes with a lesser number of reads generally receive a longer polyI tail length in comparison to genes with a higher number of reads.

To validate this analysis of tail length distributions on the overall mRNA population, the top four genes with the highest coverage found for both sample types were analyzed. With polyI+ polyA tailed and the polyA, 3' homopolymer tail lengths for all the reads in the gene were plotted along the x-axis with the density ("1" being 100% of all reads) of the reads of those tail lengths found indicated on the y-axis (FIG. 11, panel C). It was found that across these top four genes, Nanopolish calls the majority of yeast mRNAs to have an estimated poly(A)-tail of ~30-40 nucleotides with a distribution of ~10-75 nucleotides. In the polyI+ polyA samples, Nanopolish calls the majority of the poly (A)+ poly(I) tails with an estimated length of 40-50 nucleotides with a slightly wider distribution of ~15-100 nucleotides. The difference between the Nanopolish estimates after adding polyI is more like 25 nucleotides rather than our determination by biochemical methods of 50 nucleotides. This difference may be due to Nanopolish underestimating the length of polyI relative to polyA, the homopolymer that was used for calibration of Nanopolish estimates. PolyI may transit the pore more rapidly than polyA, leading to shorter estimates by almost 50%. This is supported by measuring the time traces of the different homoploymers on Gluc200A44i30, for example. The transit of 30 1 residues would be expected to take about 68% of the time it would take 44 A residues to transit if the rates were the same. Instead 130 appears to take less than half the time to transit as A44, indicating that since Nanopolish thinks it is looking at polyA and does not see polyI, in its current form it will underestimate the length of polyI tail segments. In conclusion, Cid-1 adds uniform inosine tails of 50 nucleotides to polyA RNAs to mRNAs from highly expressed genes, as observed in the median tail length estimations in FIG. 11, panel B.

Figure 12:
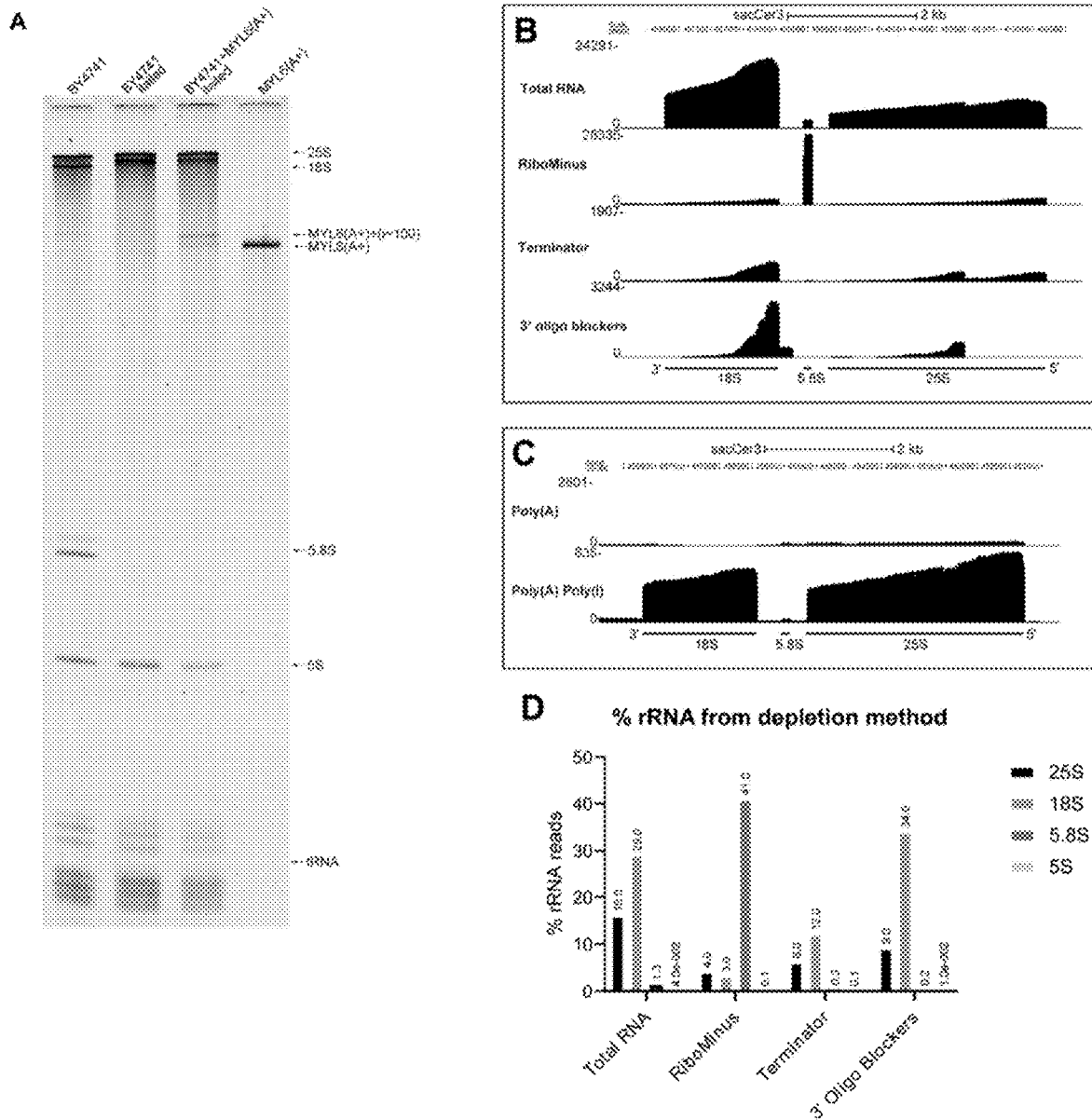
FIG. 12: Detection of non-polyadenylated RNAs is a product of representation in the sample and efficiency of tailing (Panel A) Cid-1 I-tailed Total BY4741 Yeast RNA with MYL6 control. rRNA read alignments in (Panel B) Ribosomal depletion methods and (Panel C) poly(A) enriched samples (Panel D) Graph of % of rRNA reads in ribosomal depletion methods (Panels E-F) Tail length distribution on (E) rRNA (F) snoRNA (G) ncRNA.
Figure 12:
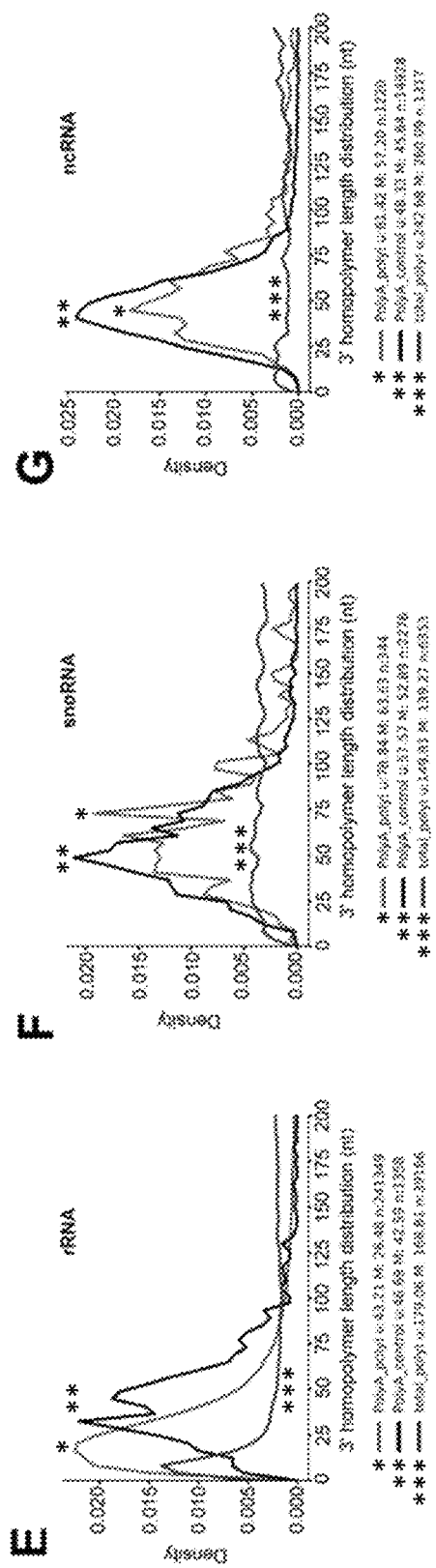

Example 8—Detection of Non-Polyadenylated RNAs is a Product of Representation in the Sample and Efficiency of Tailing As shown in FIG. 8, the ability for Cid-1 to extend both polyadenylated and non-polyadenylated RNA molecules with inosine makes it a candidate for using Cid-1 polyI-tailing to sequence a sample with both polyA and non-polyA 3' ends. To first test the ability for Cid-1 to I-tail a sample containing a mixed RNA species, yeast BY4741 Total RNA was I-tailed with a MYL6(A+) spike in control, followed by comparison to a non-Itailed Total RNA sample on a denaturing polyacrylamide gel (FIG. 12, panel A). In the un-I-tailed Total RNA lane, four bands of ribosomal RNAs were distinctly observed. Seen on the gel is the 18S from the small 40S subunit (1800 nucleotides), the three ribosomal RNAs from the large 60S subunit: 25S (3396 nucleotides), 5.8S (158 nucleotides), and the 5S (121 nucleotides), and tRNA (76-90 nucleotides). In the I-tailed lanes, Ribosomal 25S and 18S were observed to have an upward shift in size after I-tailing, and 5.8S can no longer be seen. There is an increase of products seen between the large ribosomal RNAs and under the I-tailed 18S, and there were no distinguishable changes in 5S or the tRNAs. In conclusion, Cid-1 is able to I-tail large ribosomal RNAs and 5.8S but is not able to I-tail structured RNAs like 5S or tRNA.

To test the polyI sequencing method on a mixed RNA sample, yeast BY4741 Total RNA and various ribosomal-depleted RNA were sequenced to obtain a biological sample that enriches for non-rRNA reads. Since rRNA makes up the majority of total RNA, tested was whether ribosomal-depleted RNA can be sequenced in order to better study the various non-rRNA species found in Total RNA. Tested were three different rRNA depletion methods (FIG. 12, panels B and D). Tested were the RiboMinus transcriptome isolation kit (Thermofisher), that uses a 5μ biotin-labeled lock nucleic acid probe that is specific for large rRNA for bead capture, Terminator 5'-phosphate dependent exonuclease (Epicentre) for processive digestion of 5' monophosphate ends but not 5'-triphosphate, 5'cap, or 5'-hydroxyl groups, and developed was a new technique that involves oligo blocking of the 3' end of the rRNA to prevent polyI extension. To see the number of ribosomal reads in each sample and to qualitatively see the effect of each rRNA-depletion method on the rRNAs, the reads were aligned onto the genome browser to the sacCer3 genome with the reads aligning from the 5' (left) to the 3' (right), and the number on the top of left of each panel indicates the number of reads at that height. The genome browser only contains 2 tandem copies of the repeats encoding for the rRNAs on the RDN1 locus, and alignment randomly splits the reads to both copies evenly. Shown in the figure is only one copy. Since the 5S produces few reads, that gene was omitted from the browser shot. The height of each ribosomal-depleted sample is normalized to the Total RNA reads to provide an estimate of the efficiency of rRNA depletion obtained from each method (FIG. 12, panel B). Since the 3' end of the RNA library enters the nanopore first, this ensures that the very 3' end gets read. However, in Direct-RNA Nanopore sequencing not all of the RNAs have their 5' end read out, resulting many reads not spanning the entire the gene body end to end, which is possibly caused by signal noise due to current spikes during sequencing. This explains the characteristic upward slope in coverage going from 5' to 3' (FIG. 12, panel B).

In the Total RNA sample, rRNAs accounted for 73%, while the rRNAs make up approximately 80% of the RNA in the total RNA population in yeast. There are more reads for the 18S rRNA compared to the 25S, fewer reads for the 5.8S, and the coverage shows the characteristic upward slope found in Direct-RNA Nanopore sequencing. In the RiboMinus sample, a striking finding was the high percentage of 5.8S reads, such that 41% of the total reads come from the 1.3% 5.8S in the Total RNA library. However, RiboMinus was found to be efficient in depleting the large rRNAs 18S and 25S, with an only slight increase in 5S reads. Terminator treatment before library construction creates reads that show the 5' exonuclease activity of the enzyme, with significant 5' loss for most reads, but only partial digestion of the rRNAs near the 3' ends. In the center of the 25S gene body is a GGGG sequence that may somehow promote ligation to the polyC adaptor to the RNA at that location, resulting in reads that begin at that site (this is also visible in other libraries). Terminator overall is found to be efficient at depleting rRNAs, but less efficient than RiboMinus at depleting 18S or 25S. Another method, 3' oligo blocking, was found to have a slight enrichment of 18S reads, with 34% total reads in comparison to 29% seen in the Total RNA. Since the 3' blocking oligos block the mature 3' end of the 18S, more reads were detected that started at the downstream site within the ITS, where the 3' ends of incompletely processed 18S rRNA lie. The effect of the GGGG sequence in the center of the 25S gene body that was seen in the terminator read can be seen here. Since there was no oligo designed for blocking that site, reads that start at that site and extend to the 5' end of the gene were observed. A summary of the rRNA read count findings in percentage found in each sample were graphed (FIG. 12, panel D). Close to the expected number of rRNA reads within a total RNA sample resulted and the effect of each ribosomal depletion method on Total RNA can be observed.

Since the adapter splint in Direct-RNA Nanopore sequencing only allows for sequencing of RNAs with 3' ends that can hybridize to it, non-polyadenylated RNAs in a standard polyA sequencing run should not be seen. When using the polyI method on polyA-selected RNA, residual non-polyadenylated RNAs in the sample that are missed by the standard library construction method should be detected. To test this, the reads of a typical standard polyA sequencing library and a polyI-tailed polyA library were aligned to the genome browser to the same tandem repeat of FIG. 12, panel B on the RDN1 locus (FIG. 12, panel C). In the polyA libraries, typically less <0.1% of the reads contributing to aligned rRNA reads were observed. However, when the polyA RNA was I-tailed, ~4-8% of the reads contributing to polyA RNA was generally found, which is typically within the range found for contaminating rRNA in a polyA enriched sample (cite).

In conclusion the polyI sequencing method is able to capture non-polyadenylated RNA within a sample, provided they can be I-tailed. Regarding the ribosomal depletion methods tested, it was found that every method has a different effect on the remaining rRNAs in the sample. RiboMinus is the best for 18S and 25S depletion but does not deplete 5.8S rRNA, whereas 3' oligo blockers are effective against 5.8S rRNA, and terminator is decent at depleting all rRNAs but leave substantial amounts of 3' ends undigested leading to their presence in the libraries.

In FIG. 9, observed was a pattern of Cid-1 I-tailing on non-polyadenylated RNAs where there is a heterogeneous distribution of inosine tail lengths. To ensure that Cid-1 is tailing not just the polyadenylated forms of non-coding RNAs, examined was the homopolymer tail length distribution from 0-200 nt on rRNA (FIG. 12, panel E), snoRNA (FIG. 12, panel F), and ncRNAs (FIG. 12, panel G) from the polyA, polyI-tailed polyA, and total RNA samples, with the homopolymer tail lengths plotted against the x-axis, and the fraction of the reads with that containing that size on the y-axis as "density" (density of 1=100% of all reads from that class) (FIG. 12, panels E and F). When observing the rRNA, the majority of the tail lengths for polyI-tailed polyA samples were shorter than the polyA control samples. In the total RNA sample, it was found that a large number of reads contain homopolymer tail lengths in the ~25 nt range and an even distribution from ~25-200 nt (FIG. 12, panel E). snoRNA and other ncRNA had similar distributions of homopolymer tail lengths (FIG. 12, panels F and G). The polyI tailed RNA was found to be overall ~25 nt larger than the polyA tail, but in the total RNA sample there is an even distribution of tail lengths from ~10 nt to 200 nt at a similar density. In conclusion, polyadenylated and non-polyadenylated RNAs are also being I-tailed, and they create a long stretch of I-tails with a heterogenous distribution. This supports the finding in FIG. 9 that Cid-1 creates long stretches of I-tails on non-polyA RNA and only extends a short stretch of polyI on polyA RNA.

Example 9—Examination of Nascent Transcript Structure Using I-Tailing of Chromatin Associated RNA Knowing that the polyI method works well on non-polyA RNA, sequencing a sample with mostly non-polyA and minimal polyA was of interest. Sequencing RNA transcripts still bound to RNA Polymerase II (RNPII) was of interest. RNAPII transcribes mostly pre-mRNA and several snRNAs and RNAs bound to RNA Polymerase II are considered to be nascent, as they are just coming to existence. Most of these transcripts bound to RNAPII should be pre-processed, but it is known that co-transcriptional splicing does happen (cite). Since RNAPII transcribes the RNA starting at the 5' end, the 3' end of the RNA indicates the location of the RNAPII on the chromatin as it was interrupted during transcription. Nascent RNA should give information about RNPII progression on the gene body during transcription and the rate of co-transcriptional splicing. While isolating pure nascent RNA would be ideal, it is difficult to purify pure nascent RNA from lysed cells from the endogenous biotinylated RNA and other contaminating RNAs that may stick onto streptavidin beads. Considering these factors, the sample was referenced as "chromatin-associated" RNA.

Figure 13:
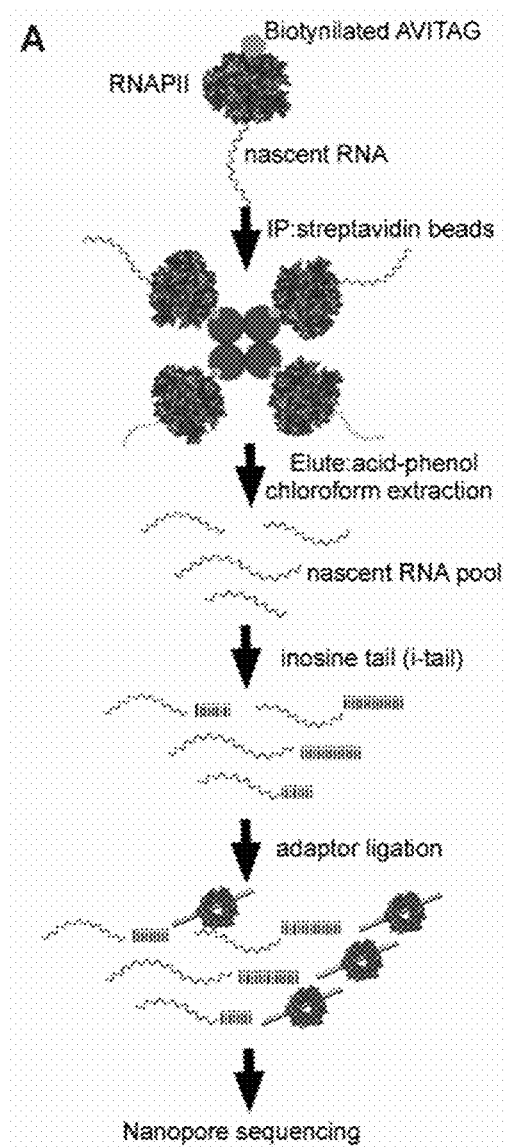
FIG. 13: Examination of nascent transcript structure using I-tailing of chromatin associated RNA. (Panel A) Purification of chromatin associated RNA using recombinant AVI-TAG RNA Polymerase II and streptavidin bead capture (Panel B) Representative aligned reads of chromatin associated RNA (Panel C) Representative aligned reads of mature mRNA found in polyA-enriched sequencing runs.
Figure 13:
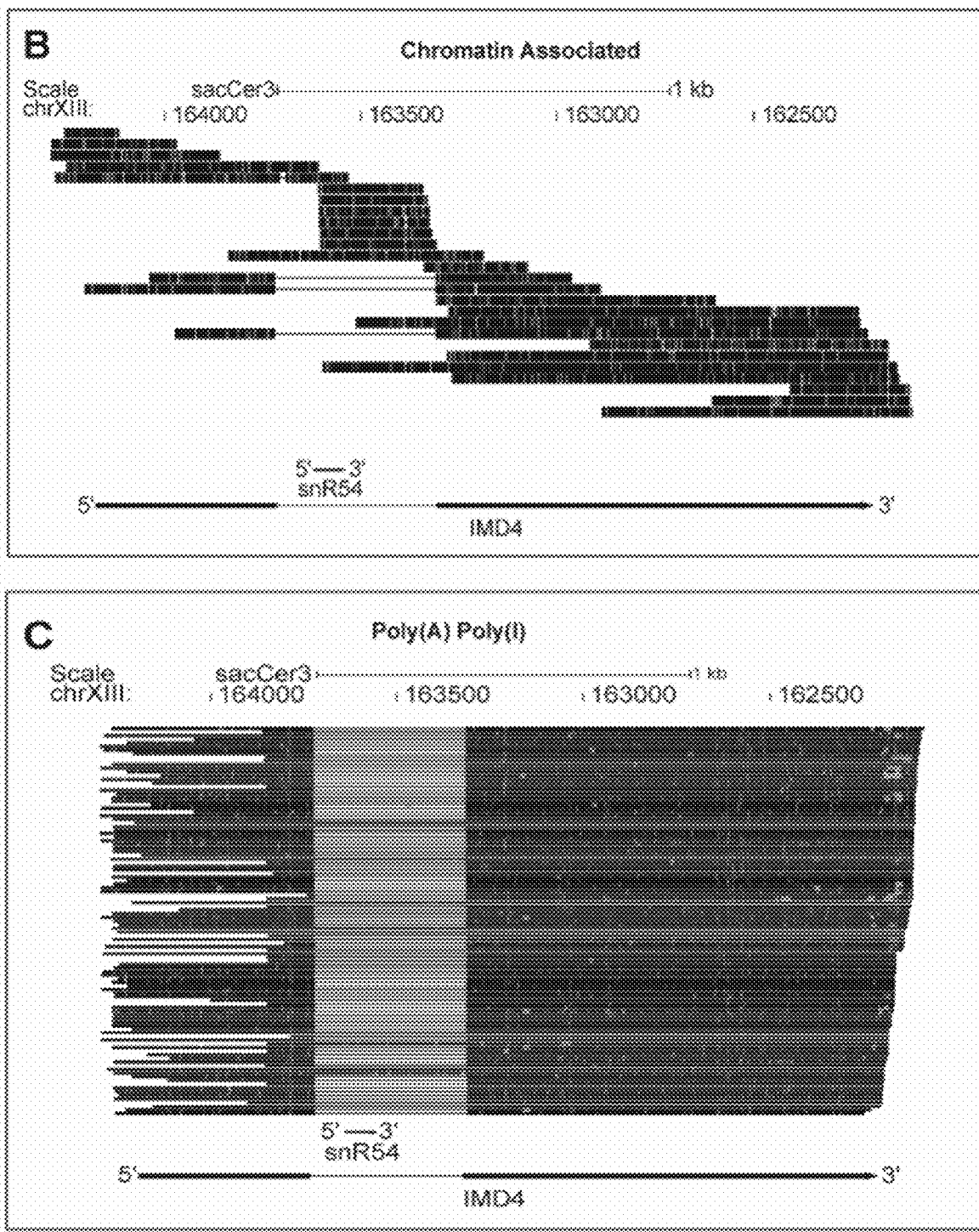

To obtain these nascent RNAs, chromatin-associated RNAs were purified by isolating chromatin from a yeast strain CKY2647 that produces a recombinant RNAPII that contains a fused small biotinylated affinity tag AviTag™, and used streptavidin beads to capture the recombinant RNPII and the chromatin associated to it. After purifying the RNA from this sample, it was sequenced using the polyI method (FIG. 13, panel A). Evidence of RNAPII transcripts was found. Shown is an example of a gene with reads aligned to the genome browser, IMD4 which contains an intronic snoRNA snR54 gene that demonstrates RNPII tracking and has evidence of co-transcriptional splicing (FIG. 13, panel B). In this chromatin-associated sample, it was seen that most of the 3' ends of these reads span across the gene body, with a few spliced reads found, and a few transcripts of the snR5 gene. When comparing the chromatin-associated IMD4 to the reads found in the polyA-enriched samples (FIG. 13, panel C), it was observed that most of those reads span across the length of the gene body with mostly processed RNA, and no snR54 transcripts. When comparing the genome browser alignments of both these runs, it was concluded that the IMD4 of the chromatin-associated RNA is nascent. The polyI method therefore can be used to study an RNA sample that does not contain any polyA.

Methods

Total RNA Extraction from Yeast

Total RNA was extracted as described previously. Briefly, S. cerevisiae BY4741 cells were grown to an A600 of 0.5 in YEPD, and 10 mL pellets were resuspended in 440 µl of 50 mM Sodium Acetate pH 5.2, 10 mM EDTA, 1% SDS and 400 µl of phenol:chloroform: isoamyl alcohol. After vortexing, the cells were incubated at 65 C for 10 minutes with intermittent 5-10 second vortexing every minute. After a 5-minute incubation on ice, the samples were added to pre-spun 2 mL Phase Lock Gel Heavy tubes (Eppendorf #955154045). After a 5-minute centrifugation at max speed, 400 µl of chloroform was added, shaken, then centrifuged again. Another 400 µl of chloroform was added, shaken, and centrifuged at full speed before transferring the top aqueous phase into a new 2 mL microcentrifuge tube. The samples were brought up to 2 mL volume with 0.3M Sodium Acetate pH 5.2 and 70% ethanol. After inversion and centrifugation, the pellets were rinsed with 70% ethanol and centrifuged before drying the pellets with a speed-vac then resuspended in nuclease-free water.

Tissue Culture and Total RNA Isolation of GM12878

GM12878 Total RNA was gifted from the Nanopore group and cells were culture and isolated as described previously.

Poly(A) RNA Selection from Total RNA

Poly(A) RNA of BY4741 and GM12878 was selected using NEXTflex Poly(A) beads (BIOO Scientific Cat #NOVA-512980) according to the manufacturer's instructions. Briefly, RNA was heated to 65 C for 2 minutes in 50% Binding Buffer at >200 µl, and chilled on ice before resuspending the prepared magnetic beads. The beads were rotated at room temperature for 5 minutes before pelleting and removal of the supernatant. Washing buffer was added, pelleted, and removed for a total of two washes. The beads were resuspended with 50 µl elution buffer, incubate at 80 C for 2 minutes and immediately pelleted before transfer of the supernatant to 100 µl of binding buffer. Eluate was heated to 65 C for 2 minutes and placed on ice before washing the beads with 200 µl of washing buffer twice. The beads were resuspended with eluate then rotated for 5 minutes in room temperature. The beads were pelleted, then washed with washing buffer twice before adding 17 µl of elution buffer, heated to 80 C for 2 minutes, then placed on the magnet for transfer of eluate to a fresh tube.

Ribosomal Depletion with RiboMinus Transcriptome Kit

Ribosomal depletion of total RNA from BY4741 yeast and GM12878 cell line using RiboMinus Transcriptome kits and Concentration Modules (Invitrogen #K155001, K155003) were prepared by bead capture according to the manufacturer's instructions. Briefly, total RNA, probe, and hybridization buffer were combined and incubated at 37 C for 5 minutes, iced, and then added to prepared magnetic beads. The beads and sample were incubated at 37 C for 15 minutes, then pelleted on a magnetic rack before transferring the supernatant to a different tube containing binding buffer and ethanol. The sample was bound to the concentration spin column then washed with washing buffer twice, then eluted with nuclease-free water.

Ribosomal Depletion with Terminator™ 5'-Phosphate-Dependent Exonuclease

Ribosomal depletion of yeast BY4741 Total RNA using Terminator™ 5'-Phosphate-Dependent Exonuclease (Epicentre) was achieved by incubating RNA (1× Terminator Reaction Buffer A, 3 µg of BY4741 Total RNA and 1unit of Terminator Exonuclease) in 20 µl volume. The reaction was incubated at 30° C. for 1 hour, then terminated with the addition of 1 µl 100 mM EDTA. The ribosomal depleted RNA was purified using 25:24:1 Phenol:chloroform:isoamyl alcohol followed by ethanol precipitation.

Ribosomal Blocking During Polyinosine Poly(U) Polymerase Tailing

To block the addition of ~50 inosine homopolymers on the 3' end of ribosomal RNAs, denaturation of RNA before itailing with poly(U) polymerase was adjusted accordingly: RNA in 0.1 mM EDTA and 0.5 pmol-4 pmol of 3' overhang or 3'stemloop oligo pools were added to a final volume of 2.95 µL, denatured at 95° C. for 2 minutes, 55° C. for 2 minutes then placed on ice for 2 minutes before proceeding to the poly(I) tailing reaction.

Polynucleotide Tailing with Poly(U) Polymerase

To add a homopolymer to the 3'end of RNA using poly(U) polymerase, RNA in 0.1 mM EDTA to a final volume of 2.95 µL is denatured at 95° ° C. for 2 minutes then placed on ice for 2 minutes. The RNA is added to a reaction containing 4 mM NTP, 50 mM NaCl, 13.5 mM MgCl2, 1 mM DTT, BSA 500 µg/ml, pH 7.9, and 1 µl of NEB poly(U) polymerase in a final volume of 7.5 µl and incubated at 37° C. for 1 hour. For library preparation the RNA was purified using SPRIselect Reagent (Beckman Coulter #B23318). The reaction was resuspended with 1.8× volume of SPRIselect Reagent and incubated at room temp for 10 minutes. The beads were pelleted on a magnet and the supernatant was decanted. The beads were washed with 70% ethanol three times, then air dried until visibly matte. The beads were resuspended in 11 µl of water and incubated in 10 minutes at room temperature, pelleted, then eluate was transferred to a new tube.

Polynucleotide Tailing with PolyA Polymerase, Yeast

To add a homopolymer to the 3' ends of RNAs using Poly(A) Polymerase, Yeast (ThermoScientific 74225Y/Z) a reaction containing (1× Poly(A) Polymerase reaction buffer, 200fmol RNA, 0.5 mM NTP) was incubated at 37° C. for 30 minutes, then two volumes of Gel Loading Buffer II (Invitrogen: AM8546G) was immediately added to stop the reaction. Reaction products were separated on 15%, 8%, 6% 8M urea denaturing PAGE.

vCID1 Expression in *E. coli*

Plasmid 10H-tev-vCID was made by standard cloning techniques using synthetic DNA. It carries a beta-lactamase gene and a colE1 origin of DNA replication in *E. coli*. *E. coli* BL21(DE3) pLysS cells are transformed with the plasmid and transformants are selected on LB (Luria Broth) agar plates with 100 μg/ml ampicillin at 37° C. overnight. A single colony is used to inoculate 50 mL of LB supplemented with 100 μg/ml ampicillin, shaking at 300 rpm overnight at 37° ° C. Overnight cultures are diluted to 1L with LB supplemented with 25 μg/ml ampicillin and grown at 37° ° C. shaking at 300 rpm to OD600=0.6. Cells are induced to express vCID by adding IPTG to 1 mM and shaking at 300 rpm for 16-18 hours at 18° C. Cells are harvested by centrifugation at 5000 rpm for 10 minutes, and cell pellets are resuspended in 10 ml of 50 mM Tris-HCl, 1 mM EDTA pH 8.0 and centrifuged again at 4° ° C. at 5000 rpm, for 30 minutes. Supernatant is decanted, and washed pellets are stored at −80° C.

vCID1 Purification

The buffers used for purification contain 50 mM NaH2PO4, 300 mM NaCl, 100 mM KCl, 1 mM DTT, 10% glycerol and various concentrations (10-500 mM) imidazole. Frozen pellets are resuspended in 14 mL of 10 mM imidazole buffer with 1 mg/mL lysozyme, 0.5 mM PMSF, then incubated on ice for 5 minutes. Cells are lysed with glass bead vortexing for 3 minutes in 15 second intervals. Cells are incubated on ice for 15 seconds between vortexing. Lysates are clarified by centrifugation at 14000×g for 1 hour at 4° C. Resulting supernatant is incubated for 30 minutes with 2.5 mL of cobalt chelate resin (pre-equilibrated in 10 mM imidazole buffer) with gentle shaking at 4° C., and then is poured into a column. The column is washed 2× with 12 mL of 20 mM imidazole buffer, and 1× with 5 mL of 50 mM imidazole buffer. Eluates are collected using 100 mM, 150 mM, 200 mM, 250 mM, 400 mM, and 500 mM imidazole buffers at 5 mL each in succession. Each eluted sample is concentrated in a protein concentrator tube (Millipore) until the total volume is <500 μL. The samples are resuspended in 10 mL storage buffer (10 mM Tris-HCl PH 7.5, 100 mM NaCl, 1 mM DTT, 0.1 mM EDTA, 50% glycerol v/v), and concentrated again until the sample volume was under 500 μL.

GLuc200130 and GLuc200A44130 Sample and Library Preparation

To prepare GLuc200130 and GLuc200A44130 samples, 15 pmol of GLuc200 RNA with 30 pmol of the appropriate bottom splint adapter for GLuc200A44 or for GLuc200, 1.4 nmols of a synthetic 5'p-15mer inosine homopolymer (Stanford PAN facility) in 10 mM tris pH 8.0, 1 mM EDTA, and 50 mM NaCl in 6 μl reaction volume was heated to 55° C. and slow cooled to 16° C. in 25 minutes. 1 μl 10×T4 ligation reaction buffer (NEB B0202S) and 2,000 units T4 DNA ligase (NEB M0202T) were added to each reaction and brought to 10 μl volume with water then incubated at 16° C. overnight. 2×RNA loading dye (NEB N0362) was added to each sample and denatured at 95° C. for 5 minutes before loading into a 10% acrylamide gel and ran for 3.5 hours at 28 watts. The gel excision was performed by post-staining with 1×SYBR gold in TBE and visualized on a UV transilluminator while cutting with a razorblade. The samples were eluted from the gel slice in 850 μl of 1×TAE buffer using a D-Tube™ Dialyzer Midi (Millipore Sigma 71507) for at least 90 minutes at 130 volts. The electro-eluted samples were precipitated with 85 μl 0.3M NaOAc and 850 μl isopropanol at −20° ° C. overnight. The next day the samples were centrifuged at 4000×g for 30 minutes, decanted the supernatant, then the pellets were washed with 70% ethanol twice with subsequent centrifugations at 16000×g for 15 minutes. The pellets were air dried for 15 minutes and resuspended in 10 μl water with yields between 25-100 ng. The libraries for each ligation product were prepared following ONT's Direct-RNA Nanopore sequencing library preparation with ~50 ng of RNA and optional reverse transcription step skipped.

In Vitro Transcription Template Generation

MYL6 and MYL6 no polyA templates were generated using linearized pUC13-MYL6 plasmid. pUC13-MYL6 was digested with Bbsl (NEB: R0539S), or Bsml (NEB:R0134S) for MYL6 or MYL6 no polyA respectively. Gluc200 and Gluc200A44 templates were generated using PCR amplification of GLuc at the first 200 nt residues at the 5'end from of pCMV-GLuc 2 Control Plasmid (NEB). The sequence was targeted using a forward primer containing a T7 promotor region, and a reverse primer that terminates the PCR product at the 3' end of the truncated GLuc sequence or the addition of 40 nt 3' polyA tail for GLuc200 and GLuc200A44 respectively. PCR amplification was obtained using Platinum® Taq DNA Polymerase High Fidelity (Invitrogen) using 1× High Fidelity PCR buffer, 0.01 μg/ul of plasmid, 0.4 mM dNTP Mix, 0.4 uM Forward Primer, 0.4 uM Reverse primer, 2 mM MgSO4, 1unit Platinum® Taq DNA Polymerase High Fidelity. PCR cycles: 94 C 30 s,/94 C 10 s, 58 C 15 s, 65 C 45 s/65 C 10 m, 4 C hold. DNA In vitro transcription templates were purified using NucleoSpin® Gel and PCR Clean-up (Macherey-Nagel) following the manufacturer's instructions.

T7 In Vitro Transcription

Templates were in vitro transcribed using the MEGAscript™ T7 Transcription Kit (Invitrogen). Reaction products were separated, and gel excised using 6% 8M urea polyacrylamide gel electrophoresis. Gel slices were rotated at 4° C. overnight in RNA Elution Buffer (0.3M NaOAc pH 5.2, 0.2% SDS, 1 mM EDTA, 10 μg/mL proteinase K). Eluted product was purified using 25:24:1 phenol:chloroform:isoamyl alcohol and ethanol precipitation.

pCp Labeling

T7 transcripts and their I-tailed counterparts were labeled with pCp [5'-$^{32}$P] Cytidine 3', 5' bis(phosphate) 3000 Ci/mmol, 10 mCi/ml. Used NEB T4 RNA Ligase 1 (NEB Cat no), 1× reaction buffer, 0.15 mM ATP, 10% DMSO, 3 mCi/ml pCp, 6 pmol of RNA, and 333 units RNA Ligase 1 (NEB M0204S). Incubated at 16° C. for ~16-18 hours. The products were cleaned up using equal amounts of 25:24:1 phenol:chloroform: Isoamyl and 0.3 mM NaOAc pH 5.2 and proceeded before ethanol precipitation.

RNAseA Digestion

RNA samples in 100 mM NaCl, 10 mM EDTA, 0.025 μg/ul RNAse A digestion were incubated at 37° C. for 15 minutes, then immediately placed in equal amounts of 25:24:1 phenol:chloroform: Isoamyl and 0.3 mM NaOAc pH 5.2 and proceeded with cleanup before ethanol precipitation.

CKY2647 Cell Harvest

CKY2647 cells were grown to an A600 of 0.5-0.8 in YEPD in 100 mL cultures. Cells were harvested at 1100×g centrifugation for 5 minutes at 4° C. Pellets were washed with 40 ml ice-cold PBS twice, then transferred to 1.7 ml Eppendorf tubes and washed with cold PBS with centrifugation at 1100×g for 5 minutes at 4° C. Supernatant was removed and pellets were snap frozen in liquid nitrogen before storing in −80 C.

CKY2647 Chromatin Associated RNA Purification

A bead column was assembled accordingly: A hole was pierced in the bottom of a 15 mL centrifuge tube with a 22-gauge needle and placed inside a 50 mL falcon tube lid with a pre-cut hole. At the 12 mL marker on the 15 mL centrifuge tube, parafilm was warped around as a stabilizer then the 50 mL falcon tube lid containing the 15 mL centrifuge was screwed back onto the bottom of the 50 mL falcon tube lid.

Working in a 4° C. room, the CKY2647 pellets stored in −80 C were thawed on ice for 5 minutes, then resuspended in 1 ml of Buffer 1 (HEPES pH 8.0 20 mM, KCl 60 mM, NaCl 15 mM, MgCl2 5 mM, CaCl2 1 mM, Triton-X100 0.8%, sucrose 0.25 mM, and freshly added 0.5 mM spermine and 2.5 mM spermidine). For lysing, the sample was added to a 2 ml Eppendorf tube containing 1 mL 0.5 mm zirconia beads, then vortexed for 1 minute with 1 minute pulses for six cycles using a pre-warmed Turbomix attachment on a Vortex Genie 2 (Scientific Industries Inc SKU: SI-0564) that was pre-warmed by running at max speed for 1 minute preceding the vortexing. The sample was transferred to the assembled bead column. For transfer of remaining lysed cells still stuck in the 2 ml tube, 1 ml of Buffer 1 was added then the tube was inverted before transferring to the assembled bead column. This process was repeated three times. The assembled bead column was centrifuged at 400×g for 6 minutes at 4° ° C. While avoiding the pellet, the supernatant at the bottom of the 50 ml falcon tube was transferred into two 1.7 ml Eppendorf tubes at 750 ml each then the pellet was discarded. The samples were pelleted by centrifuged at 2000×g for 15 minutes at 4° C. The chromatin pellets were resuspended with 800 ml of Buffer 1, then the two pellets were combined into one 1.7 ml Eppendorf tube before pelleting again by centrifugation at 2000×g for 15 minutes at 4° C. Using a pipet, the pellet was aggressively resuspended in 800 µl of Buffer 2 (HEPES pH 7.6 20 mM, NaCl 450 mM, MgCl2 7.5 mM, EDTA 20 mM, glycerol 10%, NP-40 1%, urea 2M, sucrose 0.5M, and freshly added DTT 1 mM and PMSF 0.2 mM). The sample was vortexed for 5-10 seconds, then incubated on ice for 5 minutes. The sample was centrifuged at 2000×g for 15 minutes at 4° C., then pellet was re-suspended in 800 µl of Buffer 2. The sample was centrifuged at 2000×g for 15 minutes at 4° C., then the pellet was re-suspended in 300 µl of Buffer 3 (HEPES pH 8.0, KCl 60 mM, NaCl 15 mM, MgCl2 5 mM, CaCl2 1 mM) before adding to prepared streptavidin beads for RNPII capture. (Beads were prepared by: 150 µl of streptavidin beads (NEB #S1420S) were wash with 700 µl of bead buffer (0.5M NaCl. 20 mM Tris pH 7.5, 1 mM EDTA), then applied to a magnet. Supernatant was discarded then the beads were resuspended with 300 µl of Buffer 3). The sample and beads were rotated in 4° C. for 2 hours, then the beads were washed three times accordingly: application to a magnet, discarding supernatant, re-suspending bead pellet in 500 µl Buffer 3. For RNA purification, the beads were resuspended in 500 µl of RNA Extraction Buffer (0.3M NaOAc pH 5.3, 1 mM EDTA, 1% SDS), 100 µl acid phenol, and 100 µl chloroform, then centrifuged at max speed for 5 minutes. 480 µl of the aqueous phase was combined with 1.2 mL of 100% ethanol in a fresh 1.7 mL Eppendorf tube. The samples were incubated at −80° C. for 1 hour or overnight, then was spun down at max speed for 20 minutes in room temperature. The supernatant was discarded then the pellet was washed with 600 µl of 70% ethanol by spinning down at max speed in a centrifuge for 15 minutes in room temperature. For digestion of contaminating DNA, the pellet was resuspended in 100 µl of DNAse solution (1× Turbo DNAse Buffer, 10 units TURBO DNAse (Invitrogen AM2238)) and incubated at 37° C. for 30 minutes. The sample was purified using a RNA Clean and Concentrator-5 kit (Zymo R1013) following the manufacturer's instructions and eluted in 35 µl of RNAse-free water.

Library Preparation

Purified RNA (500-775 ng) was prepared for nanopore direct RNA sequencing as follows: PolyA enriched samples were prepared using the ONT SQK-RNA001/SQK-RNA002 kit following the manufacturer's instructions. I-tailed RNA was prepared using the ONT SQK-RNA002 kit using a custom poly(C) adapter solution in place of the RTA adapter provided by the kit. Superscript IV (Thermo Fisher) was used for the optional reverse transcription for PolyA and polyI-tailed libraries. To assemble the custom poly(C) adapter, the splint was hybridized in 100 pmols top oligo, and 100 pmol bottom oligo, 50 mM Tris pH 8, 100 mM NaCl, 0.1 mM EDTA in 10 µl volume and incubating at 75° C., then immediately slow cooling at a ramp rate of 0.1° C./sec to 23° C. The hybridized adapter was diluted to 100 µl with 90 µl water, and 1 µl of adapter solution was used for polyI-tailed libraries. RNA sequencing on the MinION was performed using ONT R9.4 flow cells and the standard MinKNOW protocol script RNA001 or RNA002 recommended by ONT with one exception: collection of bulk phase raw files for the first 2 hours of sequencing then standard sequencing for ~48 hours.

Base-Calling

Guppy Base-calling Software from Oxford Nanopore Technologies, Limited, was used. Version 3.0.3+7e7b7d0 with the configuration file "rna_r9.4.1_70 bps_hac.cfg" for base-calling direct RNA. NanoFilt version 2.5.0 was used for classification of passed reads. Reads classified as "pass" had phred-score threshold of >7 and "failed" if <7. A custom script was used for fastq file "U" to "T" conversion.

Mapping

Minimap2 was used to map passed RNA reads determined by NanoFilt version 2.5.0 to (cite sacCer3, GRCh38). For yeast alignments the mapping parameters were -ax splice -uf -k10-G2000, for GM12878 alignments the mapping parameters were -ax splice -uf -k14.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

SEQUENCE LISTING

```
Sequence total quantity: 8
SEQ ID NO: 1                    moltype = AA   length = 405
FEATURE                         Location/Qualifiers
source                          1..405
                                mol_type = protein
                                organism = Schizosaccharomyces pombe
SEQUENCE: 1
MNISSAQFIP GVHTVEEIEA EIHKNLHISK SCSYQKVPNS HKEFTKFCYE VYNEIKISDK    60
EFKEKRAALD TLRLCLKRIS PDAELVAFGS LESGLALKNS DMDLCVLMDS RVQSDTIALQ   120
FYEELIAEGF EGKFLQRARI PIIKLTSDTK NGFGASFQCD IGFNNRLAIH NTLLLSSYTK   180
LDARLKPMVL LVKHWAKRKQ INSPYFGTLS SYGYVLMVLY YLIHVIKPPV FPNLLLSPLK   240
QEKIVDGFDV GFDDKLEDIP PSQNYSSLGS LLHGFFRFYA YKFEPREKVV TFRRPDGYLT   300
KQEKGWTSAT EHTGSADQII KDRYILAIED PFEISHNVGR TVSSSGLYRI RGEFMAASRL   360
LNSRSYPIPY DSLFEEAPIP PRRQKKTDEQ SNKKLLNETD GDNSE                   405

SEQ ID NO: 2                    moltype = AA   length = 391
FEATURE                         Location/Qualifiers
source                          1..391
                                mol_type = protein
                                organism = synthetic construct
SEQUENCE: 2
MGHHHHHHHH HHSSGAENLY FQSPNSHKEF TKFCYEVYNE IKISDKEFKE KRAALDTLRL    60
CLKRISPDAE LVAFGSLESG LALKNSDMDL CVLMDSRVQS DTIALQFYEE LIAEGFEGKF   120
LQRARIPIIK LTSDTKNGFG ASFQCDIGFN NRLAIHNTLL LSSYTKLDAR LKPMVLLVKH   180
WAKRKQINSP YFGTLSSYGY VLMVLYYLIH VIKPPVFPNL LLSPLKQEKI VDGFDVGFDD   240
KLEDIPPSQN YSSLGSLLHG FFRFYAYKFE PREKVVTFRR PDGYLTKQEK GWTSATEHTG   300
SADQIIKDRY ILAIEDPFEI SHNVGRTVSS SGLYRIRGEF MAASRLLNSR SYPIPYDSLF   360
EEAPIPPRRQ KKTDEQSNKK LLNETDGDNS E                                  391

SEQ ID NO: 3                    moltype = DNA   length = 5728
FEATURE                         Location/Qualifiers
source                          1..5728
                                mol_type = other DNA
                                organism = synthetic construct
SEQUENCE: 3
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accaaatgcg gtgtgaaata ccgcacagat gcgtaaggag aaaataccgc atcaggcgcc    240
attcgccatt caggctgcgc aactgttggg aagggcgatc ggtgcgggcc tcatcgctat    300
tacgccagct ggcgaaaggg ggatgtgctg caaggcgatt aagttgggta acgccagggt    360
tttcccagtc acgacgttgt aaaacgacgg ccagtgcaac gcgatgacga tggatagcga    420
ttcatcgatg agctgacccg atcgccgccc cggagggtt cgtttgaga cgggcgacag    480
atagatctga cgatagtcat gccccgcgcc caccggaaga agctgactgg gttgaaggct    540
ctcaagggca tcggtcgaga tcccggtgcc taatgagtga gctaacttac attaattgcg    600
ttgcgctcac tgcccgcttt ccagtcggga aacctgtcgt gccagctgca ttaatgaatc    660
ggccaacgcg cggggagagg cggtttgcgt attgggcgcc agggtggttt ttcttttcac    720
cagtgagacg ggcaacagct gattgccctt caccgcctgg ccctgagaga gttgcagcaa    780
gcggtccacg ctggtttgcc ccagcaggcg aaaatcctgt ttgatggtgg ttaacggcgg    840
gatataacat gagctgtctt cggtatcgtc gtatcccact accgagatat ccgcaccaac    900
gcgcagcccg gactcggtaa tggcgcgcat tgcgcccagc gccatctgat cgttggcaac    960
cagcatcgca gtgggaacga tgccctcatt cagcatttgc atggtttgtt gaaaacggga   1020
catggcactc cagtcgcctt cccgttccgc tatcggctga atttgattgc gagtgagata   1080
tttatgccag ccagcagac gcagacgcgc cgagacagaa cttaatgggc cgctaacag    1140
cgcgatttgc tggtgaccca atgcgaccag atgctccacg cccagtcgcg taccgtcttc   1200
atgggagaaa ataatactgt tgatgggtgt ctggtcagag acatcaagaa ataacgccgg   1260
aacattagtg caggcagctt ccacagcaat ggcatcctgg tcatccagcg gatagttaat   1320
gattagccca ctgacgcgtt gcgcgagaag attgtgcacc gccgctttac aggcttcgac   1380
gccgcttcgt tctaccatcg acaccaccac gctggcaccc agttgatcgg cgcgagattt   1440
aatcgccgcg acaatttgcg acggcgcgtg cagggccaga ctggaggtgg caacgccaat   1500
cagcaacgac tgtttgcccg ccagttgttg tgccacgcgg tgggaatgt aattcagctc   1560
cgccatcgcc gcttccactt ttttcccgcgt tttcgcagaa acgtggctgg cctggttcac   1620
cacgcgggaa acgtctgat aagagacacc ggcatactct gcgacatcgt ataacgttac   1680
tggtttcaca ttcaccaccc tgaattgact ctcttccggg cgctatcatg ccataccgcg   1740
aaaggttttg cgccattcga tggtgtccgg gatctccagg ctctccctta tgcgactcct   1800
gcattaggaa gcagcccagt agtaggttga ggccgttgag caccgccgcc gcaaggaatg   1860
gtgcatgcaa ggagatggcg cccaacagtc ccccggccac ggggcctgcc accatacccca  1920
cgccgaaaca agcgctcatg agcccgaagt ggcgagcccg atcttcccca tcggtgatgt   1980
cggcgatata ggcgccagca accgcacctg tggcgccggt gatgccggcc acgatgcgtc   2040
cggcgtagag gatcgagatc tcgatccgc gaaattaata cgactcacta tagggggaatt   2100
gtgagcggat aacaattcc ctctagaaat aattttgttt aactttaaga aggagatata   2160
ccatgggcca tcaccaccat catcaccatc accatcacag cagcggcgcg gaaaacctgt   2220
attttcagag cccgaacagc cataaagaat ttaccaaatt ttgctatgaa gtgtataacg   2280
aaattaaaat tagcgataaa gaatttaaag aaaaacgcgc ggcgctggat acctctgcgc   2340
tgtgcctgaa acgcattagc ccggatgcgg aactggtggc gtttggcagc ctggaaagcg   2400
gcctggcgct gaaaaacagc gatatggatc tgtgcgtgct gatggatagc cgcgtgcaga   2460
gcgataccat tgcgctgcag ttttatgaag aactgattgc ggaaggcttt gaaggcaaat   2520
ttctgcagcg cgcgcgcatt ccgattatta aactgaccag cgataccaaa aacggctttg   2580
```

-continued

```
gcgcgagctt tcagtgcgat attggcttta caaccgcct ggcgattcat aacaccctgc   2640
tgctgagcag ctataccaaa ctggatgcgc gcctgaaacc gatggtgctg ctggtgaaac   2700
attgggcgaa acgcaaacag attaacagcc cgtatttttgg caccctgagc agctatggct   2760
atgtgctgat ggtgctgtat tatctgattc atgtgattaa accgccggtg tttccgaacc   2820
tgctcctgag cccgctgaaa caggaaaaaa ttgtggatgt ctttgatgtg ggcttttgatg   2880
ataaactgga agatattccg ccgagccaga actatagcag cctgggcagc ctgctgcatg   2940
gcttttttcg cttttatgcg tataaatttg aaccgcgcga aaaagtggtg acctttcgcc   3000
gcccggatgg ctatctgacc aaacaggaaa aaggctggac cagcgcgacc gaacataccg   3060
gcagcgcgga tcagattatt aaagatcgct atattctggc gattgaagat ccgtttgaaa   3120
ttagccataa cgtgggccgc accgtgagca gcagcggcct gtatcgcatt cgcggcgaat   3180
ttatggcggc gagccgcctg ctgaacagcc gcagctatcc gattccgtat gatagcctgt   3240
ttgaagaagc gccgattccg ccgcgccgcc agaaaaaaac cgatgaacag agcaacaaaa   3300
aactgctgaa cgaaaccgat ggcgataaca gcgaataagg atccggctgc taacaaagcc   3360
cgaaaggaag ctgagttggc tgctgccacc gctgagcaat aactagcata acccccttggg   3420
gcctctaaac gggtcttgag gggttttttg ctgaaaggat cagttctgga ccagcgagct   3480
gtgctgcgca tcgtggcgta atcatggtca tagctgtttc ctgtgtgaaa ttgttatccg   3540
ctcacaattc cacacaacat acgagccgga agcataaagt gtaaagcctg gggtgcctaa   3600
tgagtgagct aactcacatt aattgcgttg cgctcactgc ccgcttttcca gtcgggaaac   3660
ctgtcgtgcc agctgcatta atgaatcggc caacgcgcgg ggagaggcgg tttgcgtatt   3720
gggcgctctt ccgcttcctc gctcactgac tcgctgcgct cggtcgttcg gctgcggcga   3780
gcggtatcag ctcactcaaa ggcggtaata cggttatcca cagaatcagg ggataacgca   3840
ggaaagaaca tgtgagcaaa aggccagcaa aaggccagga accgtaaaaa ggccgcgttg   3900
ctggcgtttt tccataggct ccgcccccct gacgagcatc acaaaaatcg acgctcaagt   3960
cagaggtggc gaaacccgac aggactataa agataccagg cgtttccccc tggaagctcc   4020
ctcgtgcgct ctcctgttcc gaccctgtcg cttaccggat acctgtccgc ctttctccct   4080
tcgggaagcg tggcgctttc tcatagctca cgctgtaggt atctcagttc ggtgtaggtc   4140
gttcgctcca agctgggctg tgtgcacgaa ccccccgttc agcccgaccg ctgcgcctta   4200
tccggtaact atcgtcttga gtccaacccg gtaagacacg acttatcgcc actggcagca   4260
gccactggta acaggattag cagagcgagg tatgtaggcg gtgctacaga gttcttgaag   4320
tggtggccta actacggcta cactagaaga acagtatttg gtatctgcgc tctgctgaag   4380
ccagttacct tcggaaaaag agttggtagc tcttgatccg gcaaacaaac caccgctggt   4440
agcggtggtt tttttgtttg caagcagcag attacgcgca gaaaaaaagg atctcaagaa   4500
gatcctttga tcttttctac ggggtctgac gctcagtgga acgaaaactc acgttaaggg   4560
attttggtca tgagattatc aaaaaggatc ttcacctaga tccttttaaa ttaaaaatga   4620
agttttaaat caatctaaag tatatatgag taaacttggt ctgacagtta ccaatgctta   4680
atcagtgagg cacctatctc agcgatctgt ctatttcgtt catccatagt tgcctgactc   4740
cccgtcgtgt agataactac gatacgggag ggcttaccat ctggccccag tgctgcaatg   4800
ataccgcgag acccacgctc accggctcca gatttatcag caataaacca gccagccgga   4860
agggccgagc gcagaagtgg tcctgcaact ttatccgcct ccatccagtc tattaattgt   4920
tgccgggaag ctagagtaag tagttcgcca gttaatagtt tgcgcaacgt tgttgccatt   4980
gctacaggca tcgtggtgtc acgctcgtcg tttggtatgg cttcattcag ctccggttcc   5040
caacgatcaa ggcgagttac atgatccccc atgttgtgca aaaaagcggt tagctccttc   5100
ggtcctccga tcgttgtcag aagtaagttg gccgcagtgt tatcactcat ggttatgcca   5160
gcactgcata attctcttac tgtcatgcca tccgtaagat gcttttctgt gactggtgag   5220
tactcaacca agtcattctg agaatagtgt atgcggcgac cgagttgctc ttgcccggcg   5280
tcaatacggg ataataccgc gccacatagc agaactttaa aagtgctcat cattggaaaa   5340
cgttcttcgg ggcgaaaact ctcaaggatc ttaccgctgt tgagatccag ttcgatgtaa   5400
cccactcgtg cacccaactg atcttcagca tcttttactt tcaccagcgt ttctgggtga   5460
gcaaaaacag gaaggcaaaa tgccgcaaaa aagggaataa gggcgacacg gaaatgttga   5520
atactcatac tctaccttttt tcaatattat tgaagcattt atcagggtta ttgtctcatg   5580
agcggataca tatttgaatg tatttagaaa aataaacaaa taggggttcc gcgcacattt   5640
ccccgaaaag tgccacctga cgtctaagaa accattatta tcatgacatt aacctataaa   5700
aataggcgta tcacgaggcc ctttcgtc                                    5728
```

```
SEQ ID NO: 4              moltype = AA   length = 8
FEATURE                   Location/Qualifiers
source                    1..8
                          mol_type = protein
                          organism = synthetic construct
SEQUENCE: 4
DYKDDDDK                                                                8

SEQ ID NO: 5              moltype = AA   length = 9
FEATURE                   Location/Qualifiers
source                    1..9
                          mol_type = protein
                          organism = synthetic construct
SEQUENCE: 5
YPYDVPDYA                                                               9

SEQ ID NO: 6              moltype = AA   length = 10
FEATURE                   Location/Qualifiers
source                    1..10
                          mol_type = protein
                          organism = synthetic construct
SEQUENCE: 6
HHHHHHHHHH                                                             10

SEQ ID NO: 7              moltype = AA   length = 10
```

```
FEATURE             Location/Qualifiers
source              1..10
                    mol_type = protein
                    organism = synthetic construct
SEQUENCE: 7
EQKLISEEDL                                                              10

SEQ ID NO: 8        moltype = AA  length = 7
FEATURE             Location/Qualifiers
source              1..7
                    mol_type = protein
                    organism = synthetic construct
SEQUENCE: 8
ENLYFQS                                                                 7
```

What is claimed is:

1. A method of adding a polymer of non-canonical nucleotides to the 3' end of a non-polyadenylated ribonucleic acid (RNA), comprising combining:
   a non-polyadenylated RNA;
   a *Schizosaccharomyces pombe* cid1 (*S. pombe* cid1) uridylyltransferase; and
   non-canonical nucleotides,
in a reaction mixture under conditions in which the *S. pombe* cid1 uridylyltransferase adds the non-canonical nucleotides to the 3' end of the non-polyadenylated RNA, thereby adding a polymer of non-canonical nucleotides to the 3' end of the non-polyadenylated RNA.

2. The method of claim 1, wherein the *S. pombe* cid1 uridylyltransferase comprises an N-terminal truncation, and wherein the amino acid sequence of the *S. pombe* cid1 uridylyltransferase is at least 80% identical to the corresponding portion of *Schizosaccharomyces pombe* cid1 (*S. pombe* cid1) (SEQ ID NO:1).

3. The method of claim 1, wherein a homopolymer of non-canonical nucleotides is added to the 3' end of the non-polyadenylated RNA.

4. The method of claim 3, wherein the homopolymer is a homopolymer of inosine, 5-methyluracil (ribothymidine), 4-thiouracil, 6-methyladenine, or 2'-O-methlyadenine.

5. The method of claim 3, wherein the homopolymer is a homopolymer of inosine.

6. The method of claim 1, wherein a heteropolymer of non-canonical nucleotides is added to the 3' end of the non-polyadenylated RNA.

7. The method of claim 5, wherein the heteropolymer comprises two or more types of non-canonical nucleotides chosen from inosine, 5-methyluracil (ribothymidine), 4-thiouracil, 6-methyladenine, and 2'-O-methlyadenine.

8. The method of claim 1, wherein the non-polyadenylated RNA is ribosomal RNA.

\* \* \* \* \*